(12) United States Patent
John

(10) Patent No.: US 8,177,726 B2
(45) Date of Patent: May 15, 2012

(54) RAPID SCREENING, THRESHOLD, AND DIAGNOSTIC TESTS FOR EVALUATION OF HEARING

(76) Inventor: Michael Sasha John, Mamaroneck, NY (US)

( * ) Notice: Subject to any disclaimer, the term of this patent is extended or adjusted under 35 U.S.C. 154(b) by 663 days.

(21) Appl. No.: 10/913,997

(22) Filed: Aug. 6, 2004

(65) Prior Publication Data

US 2005/0018858 A1    Jan. 27, 2005

Related U.S. Application Data

(63) Continuation-in-part of application No. PCT/US2004/003820, filed on Feb. 9, 2004, application No. 10/913,997, which is a continuation-in-part of application No. PCT/US03/03895, filed on Feb. 7, 2003.

(60) Provisional application No. 60/445,880, filed on Feb. 7, 2003, provisional application No. 60/354,991, filed on Feb. 8, 2002.

(51) Int. Cl.
*A61B 5/00* (2006.01)
(52) U.S. Cl. ...................................................... 600/559
(58) Field of Classification Search .................. 600/559, 600/300, 544; 607/57; 73/585; 381/60
See application file for complete search history.

(56) References Cited

U.S. PATENT DOCUMENTS

| | | | |
|---|---|---|---|
| 4,191,864 A | 3/1980 | Sopher | |
| 4,462,411 A | 7/1984 | Rickards | |
| RE34,961 E | 6/1995 | Widin et al. | |
| 5,697,379 A | 12/1997 | Neely et al. | |
| 6,118,877 A | 9/2000 | Lindemann et al. | |
| 6,175,767 B1* | 1/2001 | Doyle, Sr. | 607/57 |
| 6,196,977 B1 | 3/2001 | Sininger et al. | |
| 6,200,273 B1 | 3/2001 | Sininger et al. | |
| 6,231,521 B1 | 5/2001 | Zoth et al. | |
| 6,343,230 B1 | 1/2002 | Smits et al. | |
| 6,406,439 B1 | 6/2002 | Cohen et al. | |
| 6,602,202 B2 | 8/2003 | John et al. | |
| 6,786,873 B2 | 9/2004 | Zoth et al. | |
| 2001/0049480 A1* | 12/2001 | John et al. | 600/559 |
| 2006/0153396 A1* | 7/2006 | John | 381/60 |

FOREIGN PATENT DOCUMENTS

WO    PCT/CA01/00714    12/2001

OTHER PUBLICATIONS

Picton, Terrence, Human Auditory Steady-State Responses, 2002.*
John, M S., Brown, D., P. Muir, P., & Picton, T. W., Use of Modulated Noise in Newborn Hearing Screening. International Evoked Response Auditory Study Group (IERASG), 2003b.
Perez-Abalo, M. C., Savio, G., Gonzlez, m, Hemndez, O., Ponce de Leon, M., and Eimil, E., Hearing Screening with Multiple Frequency Steady-State Responses: A Pilot Study. International Evoked Response Auditory Study Group (IERASG), 2001.

(Continued)

*Primary Examiner* — Brian Szmal

(57) ABSTRACT

A rapid screening, threshold, and diagnostic tests for evaluation of hearing includes techniques that are particularly suited for rapid objective hearing screening and evaluation of newborns or other patients who are unable or unwilling to provide reliable subjective responses. The hearing tests may be frequency specific or may evaluate overall hearing ability without special focus on frequency-specific loss. The tests involve the use of novel stimuli, signal processing, signal analysis, and statistical techniques, including the use of ramped stimuli and evaluating the changes that these stimuli evoke in the individual's brain activity at different moments in time.

60 Claims, 9 Drawing Sheets

OTHER PUBLICATIONS

John M. S, Dimitrijevic, A., and Picton, T. W. Efficient Stimuli for Evoking Auditory Steady-State Responses, Ear and Hearing, 24(5):406-23, 2003a. John M. S., Dimitrijevic, A., and Picton, T. W. Weighted averaging of steady-state responses. Clinical Neurophysiology, 112:555-562, 2001.

John, M. S., and Picton, T. W. Master: A Windows program for recording multiple auditory steady-state responses. Computer Methods and Programs in Biomedicine, 61, 125-150, 2000.

John, M. S., Lins, O. G., Boucher, B. L., and Picton, T. W. Multiple auditory steady state responses (MASTER): Stimulus and recording parameters. Audiology, 37:59-82, 1998.

Linden R D, Campbell K B, Hamel G, Picton T W. Human auditory steady state evoked potentials during sleep. Ear Hear. May-Jun. 1985;6(3):167-74.

Norcia A M, Tyler C W. Spatial frequency sweep VEP: visual acuity during the first year of life. Vision Res. 1985;25 (10):1399-408.

Picton T W, Dimitrijevic A, John M S, Van Roon P. The use of phase in the detection of auditory steady-state responses. Clin Neurophysiol. Sep. 2001;112(9):1698-711.

Rees A, Green G G, Kay R H. Steady-state evoked responses to sinusoidally amplitude-modulated sounds recorded in man. Hear Res. 1986;23(2):123-33.

* cited by examiner

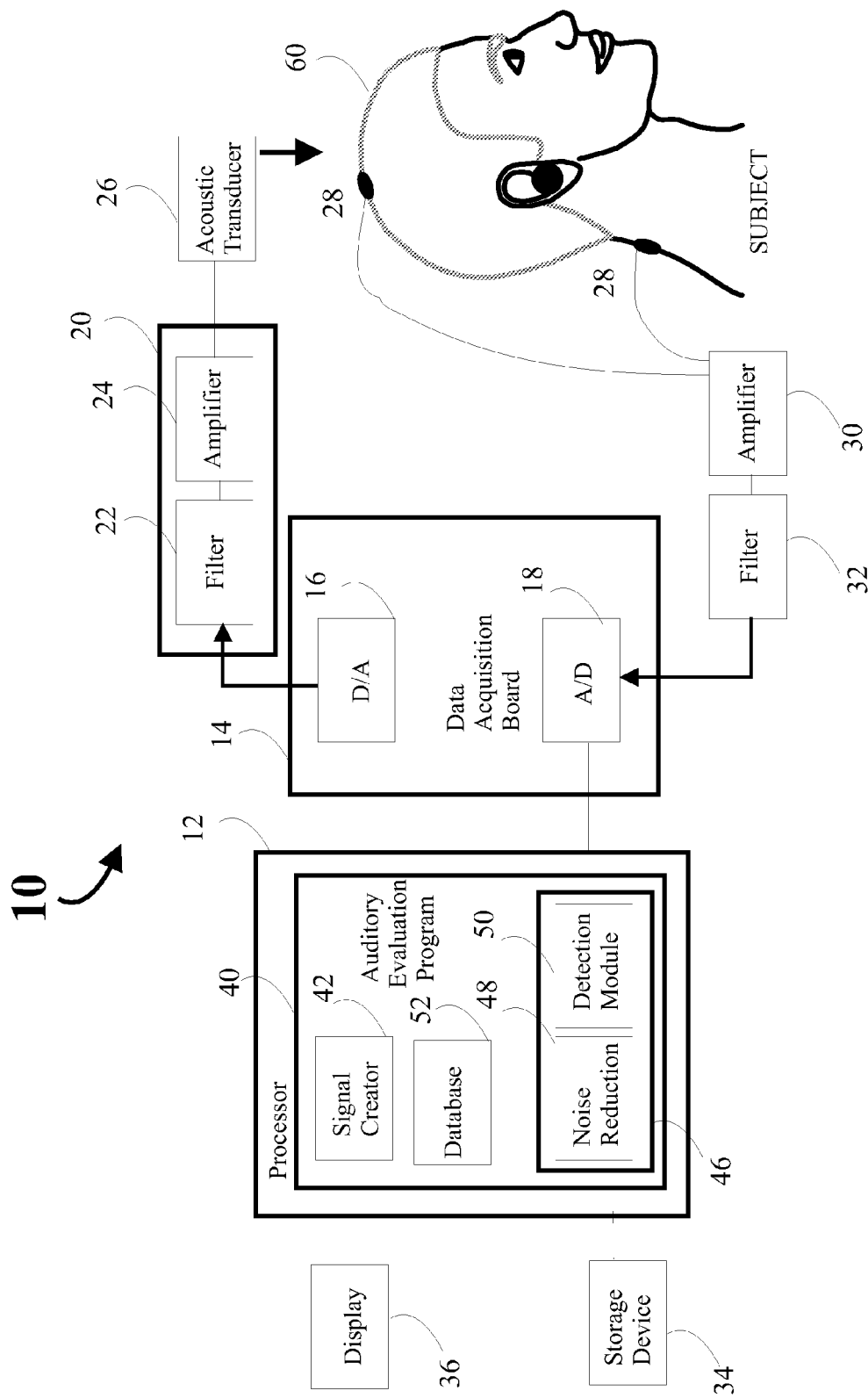

RAPID SCREENING, THRESHOLD, AND DIAGNOSTIC TESTS FOR EVALUATION OF HEARING

CROSS-REFERENCE TO RELATED APPLICATIONS

This application is a continuation-in-part of International Application No. PCT/US2004/003820, filed Feb. 9, 2004, designating the U.S. and claiming the benefit of U.S. provisional application Ser. No. 60/445,880, filed on Feb. 7, 2003, and is a continuation-in-part of International Application No. PCT/US03/03895 filed on Feb. 7, 2003, designating the U.S. and claiming the benefit of U.S. provisional application Ser. No. 60/354,991 filed on Feb. 8, 2002, the content of said applications are incorporated by reference herein.

FIELD

This patent specification is in the field of auditory assessment. It relates, in part, to the rapid initial evaluation of hearing impairment also known as "universal newborn hearing screening", but can be used for hearing screening and hearing evaluation of all ages. The hearing tests described herein may be frequency specific or may evaluate overall hearing ability without special focus on frequency-specific loss. It describes systems and methods for quickly and objectively performing screening tests, threshold tests, and other types of evaluation of the auditory system using novel stimuli, signal processing, signal analysis, and statistical techniques. It further describes systems and methods for evaluating an individual's hearing abilities by using ramped stimuli and evaluating the changes that these stimuli evoke in the individual's brain activity at different moments in time.

BACKGROUND

Hearing-impairment affects about three newborn babies per thousand. These babies must be identified as early as possible so that adequate treatment can be provided while the baby learns to hear and speak. The early detection and treatment of hearing loss helps the hearing-impaired child to communicate effectively, and benefits society since this individual then requires less in the way of support. Governments in Canada, the USA and Europe have therefore instituted programs for universal newborn hearing screening (UNHS). Infants cannot reliably respond to sound—one cannot ask a baby if it can hear a sound. Screening must therefore be performed by non-behavioral/non-subjective measures such as by measuring the response of the ear or the brain to sound. The ear's response can be measured using "otoacoustic emissions" and the brain's response can be tested using the "auditory brainstem response" (ABR). Both tests have their drawbacks. The otoacoustic emissions are fast, but do not check whether the brain is receiving information from the ear. The ABR tests take longer to record than would be optimal for a screening test.

Currently, the click-evoked auditory brainstem response (c-ABR) is the standard test for screening and evaluating infant hearing, but this is often not automatic and is not frequency-specific. While this test will detect gross hearing loss, it may not detect hearing loss at specific frequencies that are important to the development of speech and language, may require a long time in some cases, and may not have high accuracy. Tone-evoked ABRs (t-ABR) can be used to assess frequency-specific thresholds, but this testing procedure takes too long to be used routinely and the results can not be evaluated objectively and automatically by computer (Stapells, 1997). The use of otoacoustic emissions (OAEs) is popular for quick screening of normal auditory function, but will only detect peripheral loss and, while OAE methods can detect hearing impairment, these techniques cannot be used to determine the actual extent of the hearing loss. Frequency-specific audiometric techniques that are rapid and accurate are therefore important for detecting auditory thresholds and fitting hearing aids in infants, or other patients, who are unable to easily provide reliable indication of their hearing abilities.

There are two main types of tests that may be implemented by an audiologist: screening tests and threshold tests. These tests can be carried out for either frequency-specific stimuli, or for non-frequency specific stimuli. For example, current UNHS tests are done using non-frequency-specific click stimuli which contain energy at many frequencies. These tests indicate whether or not an infant has a minimal acceptable level of hearing and usually provide a simple pass/fail result. In the case where an individual fails a screening test (hearing thresholds are elevated), a threshold test can provide a further assessment of auditory abilities. In a threshold test, an individual's hearing is tested at successive intensity levels in order to determine the thresholds of a patient (i.e., the minimum level at which a patient can hear a sound). There is a need for objective frequency-specific threshold tests that can be performed relatively quickly since conventional objective hearing threshold tests require on the order of 30-40 minutes for obtaining a hearing threshold at multiple frequencies. This amount of time prevents the test from becoming clinically feasible in some cases because, for example, a sleeping infant may wake up and start crying, which makes testing impossible.

SUMMARY

The proposed system and methods for performing rapid hearing screening and evaluation rely on novel stimuli, testing procedures, signal processing techniques, and statistical methods that allow the testing to occur more rapidly, accurately, and thoroughly than currently available methods. The system may be used to test hearing in animals or humans of all ages, including infants, elderly people, workers claiming compensation for noise-induced hearing loss, and any other individuals who are unable or unwilling to provide reliable behavioral responses during conventional hearing tests. The system and methods may be used as a rapid screening test, providing a pass/fail result, and can also be used to provide threshold information or other information about an individual's auditory system. The stimuli and methods can be used for testing the aided and unaided hearing abilities of a patient.

The inventor has previously described novel techniques to evaluate frequency-specific hearing thresholds by recording the brain's response to frequency-specific sounds using auditory steady-state responses (ASSR), which are also known as steady-state auditory evoked potentials (SS-AEPs). These techniques provide a fast and accurate assessment of hearing at specific frequencies (John et al, 1998; John et al 2000; PCT/CA 01/00715). The new set of techniques described herein can accomplish rapid screening and hearing evaluation (both for frequency-specific hearing abilities & gross hearing abilities) using methods that are faster and more accurate than those previously described both by the inventor and by others. The new set of techniques described herein can also evaluate hearing capacities of the auditory system, such as tuning curve characteristics, not measured by the methods described previously.

In one embodiment, a rapid and non-frequency specific hearing screening test is described which uses modulated noise stimuli and periodic stimuli (e.g. clicks) which are presented at a constant intensity and at sufficiently rapid rates so that SS-AEPs can be evoked within the patient's EEG. In an alternative embodiment, a single modulation stimulus or band-pass noise stimuli are used to provide a rapid hearing screening test which provides both non-frequency-specific and frequency-specific information. In another alternative embodiment, threshold tests are described in which ramping stimuli and time-frequency analysis techniques are used in order to determine non-frequency specific hearing thresholds. In yet another alternative embodiment, ramping stimuli and time-frequency analysis techniques are used in order to determine frequency specific hearing thresholds. Although these ramping stimuli tests may be used to rapidly provide hearing assessment for at least one stimulus at many intensities, thereby providing threshold information, this information can also be used for screening purposes. In another alternative embodiment, ramping stimuli are used to reliably determine the physiological modulation transfer function of an individual. This information can be used, for example, to determine optimal modulation rates are for an individual. Optimal modulation rates are rates that evoke responses with good signal-to-noise levels. These rates can be used in order to increase the efficiency, sensitivity, and specificity of hearing evaluation using subsequently performed audiometric tests. In another alternative embodiment, ramping stimuli are used to determine the fine structure of the audiogram and tuning characteristics of an individual's auditory system. In the embodiments which rely on evoked potentials which change over time due to a ramping stimulus ("R-AEPs") and time-frequency analysis, methods such as "threshold series" and "homogeneity criteria" may be used to improve the accuracy and clinical values of the tests. In the embodiments which rely on SS-AEPs and frequency analysis, using methods such as "significance series" and "homogeneity criteria" may be used to improve the accuracy and clinical value of the tests. These new techniques can be used to test one ear at a time, or can be used to test both ears simultaneously. In addition, several stimuli can simultaneously be presented within each single ear.

The inventor has published a series of scientific publications on using multiple modulated tones to efficiently obtain frequency-specific hearing thresholds. These methods are known as the Multiple Auditory Steady-State Response (MASTER) technique (John et al., 2000). The testing methods described herein are novel from and offer advantages over those used by the MASTER technique. Methods are described to perform screening tests which use SS-AEPs evoked by stimuli that are relatively non-frequency specific. Because responses to non-frequency specific stimuli, such as clicks and amplitude modulated noise (e.g., broadband or band-pass noise) are larger than responses to frequency-specific stimuli, the novel methods described here can be used in tests which are faster and more reliable, and which can occur at lower intensities than permitted by the prior art techniques. These qualities are advantageous for rapid screening tests.

In one embodiment a screening test is described which uses modulated noise stimuli. SS-AEPs evoked by amplitude modulated noise have been investigated (e.g., Rees et al., 1986). The Inventor (John et al, 1998), used amplitude modulated noise and showed that the evoked steady-state responses were larger than those evoked by amplitude modulated tonal stimuli presented at fairly high intensity levels. However, until several experiments were done by the Inventor using lower intensities and rapid testing times, as are reported here, it was not understood that i) the increased size of these responses, would also be robust at low intensities, ii) the size of these responses would be between approximately 200-400% the size of the responses found with tonal stimuli, iii) the size of these responses would be sufficiently larger than the background EEG-noise levels, even at low intensities, to be easily detectable, and iv) unlike frequency-specific tonal stimuli, the responses would be reliably evoked in a short amount of time in all individuals with normal hearing, and thereby permit rapid and reliable detection of the responses. It is these qualities that enable these stimuli to be used in a rapid and objective screening test. SS-AEPs are normally recorded to modulated tonal carriers that sometimes require quite of bit of time to become significant, and are therefore not appropriate for a rapid screening test.

Additionally, click stimuli can also be used in an SS-AEP based screening test using the new methods. Click stimuli have been used for screening for many years, but were not presented at sufficiently rapid rates to generate SS-AEPs. Importantly, unlike conventional c-ABR screening tests, when clicks are used to generate SS-AEPs in accordance with the present disclosure, the clicks must occur at a repetition rate that causes the time between click stimuli to be an integer sub-multiple of the epoch length. Additionally, creating various types of transient stimuli which are characterized by this integer sub-multiple repetition rate is another aspect of the methods described herein.

In accordance with this disclosure a set of methods is described for using ramping stimuli to generate R-AEPs which are analyzed in the time-frequency domain ("ramping techniques") to accomplish different types of objective audiometric tests. Ramping stimuli (also referred to as "ramp stimuli", "ramped stimuli", or "R-AEP stimuli"), are stimuli for which a particular characteristic is changed or "ramped" over time in an intentional manner. R-AEPs can be evoked by either frequency specific or non-frequency specific stimuli. In one embodiment, a ramping technique utilizes an intensity ramp and provides information about response magnitude at several intensity levels. Similar to the use of a ramping technique or "a sweep technique" in the visual modality which was used to test visual acuity (Norcia and Tyler, 1985), ramping techniques have been attempted for auditory stimuli. Linen et al presented ramping stimuli at intensities which ramped from −21 to 60 SL (Linden et al, 1985), but concluded that the variability in the estimates of threshold was too large for ramping stimuli to be incorporated into an accurate clinical method. However, the present disclosure provides signal analysis and signal processing methods which are novel and offer advantages over those of the prior art by using methods which decrease the variability of both the noise and signal estimates derived from the a patient's EEG data, and by providing methods for estimating the reliability of threshold estimates derived during the testing procedures. For example, methods are described for rejecting data and for substituting this rejected data with acceptable data. Further, methods are described for increasing the utility of the data by dynamically changing the ramping stimuli during the testing procedure according to the characteristics of the R-AEPs. Methods are also described for testing the reliability of threshold estimates. Accordingly, the ramping techniques of the present disclosure describe objective audiometric tests that rely upon novel methods concerning testing protocols, stimulus presentation, data collection, signal processing, and data analysis (e.g. determination of thresholds) which lead to more accurate and more efficient testing methods.

An advantage of the R-AEP tests are that they may provide a more accurate assessment of threshold than SS-AEP tests which iteratively test at different intensities. For example if a subject is able to produce an evoked response to a stimulus presented at 48 dB, but the stimulus is tested in 10 dB steps, e.g., at 50 dB and then at 40 dB, then the threshold estimate will be off by 8 dB. Decreasing the step size may give more accurate estimates of threshold, but will also lengthen test times.

A system and methods are provided that utilize the aforementioned techniques to measure hearing quickly and automatically. The methods can be completely objective, which means that subjective responses are not required from the person being tested and subjective interpretations are not required from the clinical personnel conducting the test. The system presents acoustic stimuli to a patient, and concurrently records brain activity ("EEG") with the premise that if the brain activity is altered by the stimuli, then the individual can hear the stimuli being tested. The system and methods may be realized through both hardware and software components, although different embodiments may rely more upon hardware or software. The different methods described herein may be realized as software modules of the system.

In particular, the present disclosure provides a system and a set of methods for performing objective audiometry by, for example, choosing test protocols, presenting stimuli while simultaneously acquiring EEG data, increasing data quality by modifying and organizing the EEG data within the data set, performing signal processing and analyzing the EEG data in the frequency domain or time-frequency domain to generate result data which can include an amplitude spectrum, a spectrogram, estimates of evoked responses such as SS-AEPs and R-AEPs and estimates of the background EEG-noise levels, and using the result data to provide Test Results. The system further enables displaying the results of ongoing testing and the final Test Results as well as the storage of the raw data and Test Results for subsequent viewing and/or analysis. The software is also adapted to carry out tests of data quality and consistency in order to determine if the results are meaningful and reliable.

Particular types of stimuli are disclosed which increase the amplitude of the resulting responses or offer other advantages over alternative stimuli when used in a screening (or threshold) test. These stimuli include amplitude modulated broadband noise, and band-pass noise (including narrow-band noise) which can be either modulated or un-modulated. These stimuli also include ramped acoustic stimuli that are characterized by continuously changing characteristics, for example, time-varying intensity. These stimuli also include multiple intensity stimuli in which at least 2 intensities are simultaneously tested. These stimuli may be formed by using either different or the same modulation/repetition rate for each carrier signal of the stimulus.

The systems and methods further comprise a database which contains normative data which may be population normative data or self norm data (prior data collected from a subject).

Further objects and advantages will be apparent from the following description, taken together with the accompanying drawings.

BRIEF DESCRIPTION OF THE DRAWINGS

For a better understanding of the written description and to show more clearly how it may be carried into effect, reference will now be made, by way of example, to the accompanying drawings which show preferred embodiments and in which:

FIG. 1a is a block diagram of a preferred embodiment of a system;

DETAILED DESCRIPTION

Figure 1B:
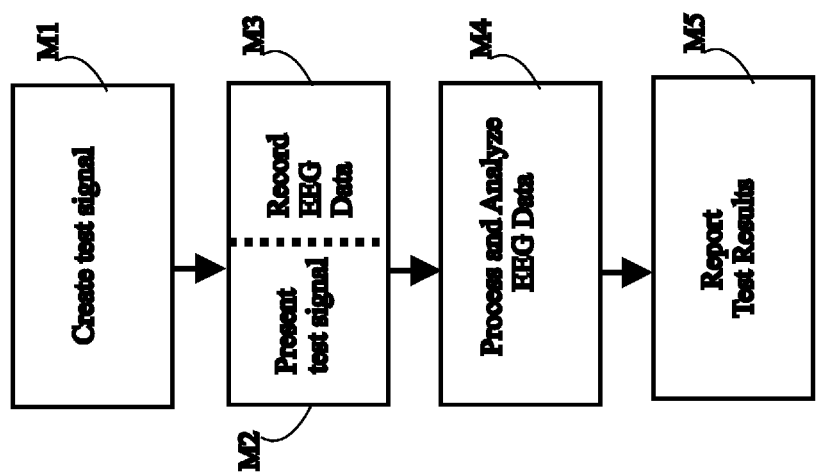
FIG. 1b is a flow diagram illustrating a general objective auditory test methodology.

A system and methods are disclosed, in accordance with the present invention, for using SS-AEPs and R-AEPs to achieve objective audiometry by relying upon novel stimuli, test procedures, data criteria, signal processing, statistical, and data analysis techniques. A set of methods is disclosed for using the system to rapidly screen for hearing pathology, to obtain estimates of hearing threshold, or to evaluate other characteristics of the auditory system. The basic hardware and software components of the system will be discussed first. Methods for hearing evaluation, such as for screening and for threshold estimation will then be discussed. These techniques utilize novel types of acoustic stimuli, data analysis, noise reduction and response detection methods. Methods for objective audiometric testing based on R-AEP stimuli will be discussed with respect to obtaining auditory thresholds and other types of information about the auditory system. The system and methods described herein enable objective auditory testing to be achieved quickly and accurately. This allows the test to be performed when an infant is sleeping and allows many infants to be tested in a short time. Several fundamental methods of achieving a faster test are by making the signal larger, making the noise background smaller and less variable, modifying the test dynamically based upon response data and interpolating from existing data. New methods which address each of these areas are employed.

Hardware and Software Components

Referring now to FIG. 1a, shown therein is a system 10 for performing objective audiometry that includes a processor 12, a data acquisition system 14 that can be a board having a digital to analog converter (DAC) 16 and an analog to digital converter (ADC) 18, an audiometer 20 having stimulus filtering circuitry 22 and stimulus amplifier circuitry 24, a transducer 26, sensors 28, response amplifier circuitry 30, response filter circuitry 32, a storage device 34 and a visual display 36. The processor 12 contains an auditory evaluation program 40, which is realized using hardware or by a software program, comprising a signal creator module 42, and an analysis module 46 having a noise reduction module 48 a detection module 50, and a database 52 having a plurality of normative values.

A personal computer (PC), for example a Pentium 750 running Windows 2000, may provide the processor 12, storage device 34 and display monitor 36. The auditory evaluation program 40 is run on the PC and the database 52 can be stored in the memory and storage device of the PC and can communicate with the auditory evaluation program 40. Alternatively, these components may be effected on a laptop, a programmable handheld computing device, such as a palmtop, or a dedicated electronics device.

The objective audiometric test system 10 can be used to assess the auditory system of a patient 60 by presenting acoustic stimuli to the patient 60, while simultaneously amplifying and digitizing sensed potentials into EEG data (This can also be referred to in this application as "data", "response data", or "evoked response data"). The EEG data is then processed and statistically evaluated to determine if this data contains evoked responses (these can be termed, "signals", "responses", "ASSRs", "auditory steady-state responses", "SS-AEPs", "ramping evoked responses" "RAMPERs" or "R-AEPs"). For example, signal processing may show the responses that are statistically significantly different than the background EEG-noise levels. The design of the objective audiometric test system 10 follows clear principles for carrying out test protocols, generating the acoustic stimuli, acquiring response data, performing signal processing on response data to ensure that data which does not meet specific criteria are rejected thereby providing the frequency-domain or time-frequency domain signal processing routines with high quality accepted data epochs in order to generate "result data" (e.g. a spectrogram, amplitude plot, phase plot, statistical characteristics of signals and noise levels such as mean and standard deviation, threshold series data, significance series data), statistically and objectively evaluating the result data to obtain "summary data" (e.g., statistical probability of the presence of a response, results of the application of statistical conditional criteria, estimates of the auditory function of an individual such as frequency-specific intensity thresholds, results of regression operations) and using the summary data to produce "test results", which can include the summary data, but which also include results such as Pass/Fail status.

The data acquisition system 14 can be a commercial data acquisition board (e.g., AT-MIO-16E-4) available from National Instruments, or a comparable alternative. The data acquisition system 14 allows for the output of data (e.g., the stimuli) via the DAC 16 as well as the input of data via the ADC 18.

The output from the DAC 16 is sent to a signal conditioner such as an audio amplifier or audiometer 20 which is under the control of the processor 12. The audiometer 20 acts to condition the stimulus that is presented to the patient 60 via the stimulus filter circuitry 22 and the stimulus amplifier circuitry 24. Rather than using the audiometer 20, functionally similar amplifying/attenuating and filtering hardware and/or software can be incorporated into the objective audiometric test system 10 to control the intensity and frequency content of the stimulus and the operational settings (e.g., band-pass, filter characteristics, gain) for both the filtering and amplifying circuitry. The stimulus is presented to the patient 60 via the transducer 26 which may be at least one free-field speaker, headphone, insert earphone (e.g. ER3A from Etymotics Research) or bone conduction vibrator. The transducer 26 allows the steady-state or ramping stimulus to be presented to the left and/or right ears of the patient 60.

While the stimulus is presented to the patient 60, the EEG is substantially simultaneously sensed using sensors 28 which are typically electrodes. For example, one active electrode can be placed at the vertex location of the head of the patient 60, one reference electrode can be placed on the neck of the patient 60 and a ground electrode can be placed at the clavicle of the patient 60. Other configurations for the electrodes are possible as is commonly known to those skilled in the art. It is also possible to use more electrodes than are shown in FIG. 1a.

The sensed EEG data is routed to the response amplifier circuitry 30, which is typically a differential amplifier, for amplifying the sensed EEG data to a level that is appropriate for the input range of the ADC 18. The response amplifier circuitry 30 may use a gain of 50,000. Alternatively, the response amplifier circuitry 30 may be a programmable amplifier that provides a variable gain that may be under the control of the auditory evaluation program 40. The amplified sensed EEG data is then sent to the response filter circuitry 32 which filters the amplified sensed EEG data such that sampling can be done without aliasing by the ADC 18. The response filter circuitry 32 may have a band-pass of 1-300 Hz. However, the band-pass range can change depending upon various considerations such as the characteristics of the stimuli (e.g. modulation rates) that are being used for testing. The ADC 18 digitizes the filtered amplified EEG data at a rate of approximately 1,000 to 5,000 Hz, or another suitable rate, provided that the upper limit of the band-pass range of the response filter circuitry 32 is set so that the Nyquist rate is not violated as is well understood by those skilled in the art.

The objective audiometric test system 10 can be embodied in various ways. For example, multiple outputs may also be used (e.g. an eight channel DAC) to create the acoustic stimuli that are presented to each ear of the patient 60. This would allow some components of the stimulus to be easily dynamically manipulated in real-time independently from the others. The auditory evaluation program 40, may realize its novel testing methods and test protocols using a software program, created with any modern programming language such as LabVIEW, MATLAB, or C or), or in a combination of these languages, since these languages allow calls to external routines (for example, LabVIEW can call a MATLAB routine). The software platform can be similar to the MASTER (Multiple Auditory Steady-State Response) system (John & Picton, 2000; www.blsc.com), which utilizes a graphical user-friendly interface based upon a series of interactive screens which allow users control the auditory evaluation program 40, for example, to create and load test protocols and their parameters, to view and modify stimuli, and to view, on the visual display 36, the incoming evoked response data in real time in both the time and frequency (or time-frequency) domain, and to view summary results and test results for the patient 60. The auditory evaluation program 40 can also save the test results and recorded EEG data on the storage device 34, and also allows the test results to be printed by a printer (not shown). The auditory evaluation program 40 enables the user to choose different methods of viewing, storing, combining and analyzing data. The data can include either the raw data or averaged data, and can include the responses from a single patient or from a plurality of patients. Portions of the data may also be subtracted from other portions, in order to enable the user to calculate, for example, derived-band responses.

The auditory evaluation program 40 controls test signal generation ("the stimuli) via the signal creator module 42. The auditory evaluation program 40 also allows the user to select from a variety of pre-defined objective audiometric tests "test protocols". The settings or "parameters" of the test protocols may be modified by the user, and in order to define, for example, the stimuli (e.g., modulation rate, carrier frequencies, intensities, characteristics, such as range, of a ramping stimulus), maximum duration of the test, criteria to be used during the test (e.g., homogeneity criteria), signal analysis methods to be used by the test (e.g., weighted averaging, method of rejecting/substituting data epochs), and other features of the test. The signal creator module 42 allows the creation of the time series waveforms that are used as the acoustic stimuli. The auditory evaluation program 40 also controls analog-to-digital conversion and digital-to-analog conversion according to the protocol of the auditory test that is being performed. The auditory evaluation program 40 comprises a plurality of modules that are not all shown in FIG. 1a to prevent cluttering the Figure. For example, there are modules for reviewing raw data that is read from disk and for viewing test results for each frequency tested and at several intensities, for example, in an audiogram. Each of the different test protocols which rely on the methods described herein can be realized in a different software module. The auditory evaluation program 40 enables the test to be accomplished by performing the data analysis/management, signal processing, statistical processing, in order to generate summary results and test results During an auditory test, the auditory evaluation program 40 analyzes the sensed evoked response data via the analysis module 46 that includes the noise reduction module 48 and the response detection module 50. The noise reduction module 48 may employ weighted averaging, time averaging and/or various types of artifact rejection (which will all be described later in more detail) on the evoked response data. The evoked response data is then analyzed by the detection module 50 to determine whether at least one evoked response is present within the sensed evoked response data. The detection module 50 may employ a phase weighted t-test, or other methods which will later be described in more detail. In the case of R-AEPs, the detection module 50 may also be used to determine if a reliable threshold estimate has been detected.

The auditory evaluation program 40 also communicates with the database 52 which contains a plurality of normative data values, which were generated from normal populations, which relate to a variety of parameters for audiometric testing using the different test protocols. For instance, the database 52 includes normative mean and variance values for measures such as phase data which can be used during a phase-biasin t-test. The database 52 can also include normative values, according to test protocols (e.g., relating to different intensities of the stimuli and different modulation/repetition rates), for such measures as the amplitudes and phases of evoked resposes, response amplitude vs. intensity curves (slopes of R-AEPs over time, or SS-AEPs at different intensities) and other mesures, which can be used to help detect and evaluate SS-AEPs or R-AEPs and to determine whether these are indicative of normal or abnormal hearing. The database 52 can also include normative data which is a self norm data. Self norm data is derived from the individual being tested, and may be obtained, for example, from prior data obtained for that patient to stimuli which may have be presented at a different intensity, or from data recorded earlier in the current test (e.g., to the current stimuli), or from responses to other stimuli in the test being conducted. The normative data which are organized in terms of the patient's characteristics such as age, sex. The database 52 can also contain normative values for background EEG-noise levels, and these values can be defined differently for different test durations. The database 52 can also contain normative testing durations which are required for the responses evoked by stimuli used in different test protocols to become significant for a proportion, e.g., 80%, of the population.

The auditory evaluation program 40 interacts with the signal creator module 42 to permit the user to select a particular type of acoustic stimulus and control the parameters of the selected acoustic stimulus. In addition to the amplitude and frequency modulated stimuli that are described in PCT patent application No. PCT/CA 01/00715, and the parameters that are available for modification (e.g., modulation rate, carrier frequency), the signal creator module 42 allows for the creation of un-modulated or modulated noise which may be band-limited, and allows for the creation of periodically repeating transient stimuli and the creation of ramp stimuli by allowing ramp functions to be defined. Ramped functions are defined by parameters such as amplitude range of the ramping function and duration of the ramping function (which both define the rate of change over time), as well as the ramping function shape (e.g., linear, logarithmic, smooth or stepped, symmetrical and non-symmetrical). Additionally, the upward or downward portion of a ramping function may consist of more than one slope. For example, when the intensity of the stimulus is the characteristic being ramped, and a dual slope function is used, the slope of the ramp may be smaller while the intensity of the stimulus is lower and may change to a steeper slope when the ramping function traverses the higher intensity range. If dual slope functions are used, then two threshold estimations may be computed separately, using the R-AEP responses evoked by the two separate portions of the ramp.

Once the stimulus parameters are chosen, the signal creator module 42 automatically adjusts them in order to ensure that certain rules are followed. For instance, the signal creator module 42 ensures that an integer number of cycles of the modulation signal fit in the output buffer of the DAC 16 and the input buffer of the ADC 18. In the case of transient stimuli, the repetition rate is chosen so that the duration of the stimulus combined with the post-stimulus interval that occurs prior to the next stimulus presentation results in a duration which is an integer sub-multiple of the duration of an input/output buffer (i.e., of the epoch length). This is important to avoid spectral spreading in the generated acoustic stimulus as well as to avoid spectral spreading in the sensed EEG data which are digitized by the ADC 18. The signal creator module 42 may also be used to present test signals to the patient 60 with constant peak-to-peak amplitudes or constant RMS amplitudes, whereby the amplitude of the envelope of the test signal is increased to compensate for the modulation depth of the stimuli (e.g., 80% amplitude modulation). Any stimulus (e.g., steady-state noise, amplitude modulated tones, and transient stimuli) which is able to produce an SS-AEP can be referred to as an "SS-AEP stimulus". Any stimulus for which a given parameter (e.g., intensity, modulation rate, carrier frequency) is ramped over time in order to produce an R-AEP, can be referred to as an "R-AEP stimulus". The signal creator module 42 is able to create many types of SS-AEP stimuli and R-AEP stimuli, as well as other types of stimuli (e.g. un-modulated masking stimuli), for example, according to user specifications, dynamically, according to the procedures of the testing methods as will be described, according to specifications of different test protocols which may be loaded from disk, as well as according to specifications which are defined within the auditory evaluation program 40 for the various tests described.

The signal creator module 42 can create a variety of test signals that can be used to evoke the SS-AEPs and R-AEPs. These test signals can include amplitude modulated noise (including broad-band, band-pass, & narrow-band noise), transient stimuli, single-modulation frequency stimuli, and ramp stimuli. The signal creator module 42 can also generate stimuli such as high-pass, low-pass, or band-pass noise, all of which can be either modulated or un-modulated, which can function as test signals or as "masking" stimuli. In the case of band-pass noise, the signal creator module 42 may allow the user to adjust the band-pass and band-stop characteristics, including the roll-off. The signal creator module 42 can also generate a train of rarefaction, condensation, or alternating polarity clicks, which repeat at an interval that is a sub-multiple of the epoch length.

The auditory evaluation program 40 permits the user to define test protocol parameters such as the sampling rate of the ADC 18, the sampling rate of the DAC 16 (which must be a multiple of the A/D rate) and the epoch duration (i.e. the size of the input buffer contained in the ADC 18). The user may also define an artifact rejection technique and associated parameters, calibration coefficients which adjust the amplitude and phase of the estimated responses based upon recording parameters such as the filter settings, and choose various signal processing options related to the processing of the evoked potential data The artifact rejection level may be based one or more criteria. For example, artifact rejection criteria may include an absolute threshold value, the average amplitude of a high-frequency range of the evoked potential data, or values based upon certain characteristics such as standard deviation of the power in a frequency range of the evoked response data collected for that patient earlier in the recording.

Prior to running a test, the auditory evaluation program 40 permits the user to view the stimuli that will be presented to the patient 60. During a test, the user may view the sensed EEG data for the current epoch that is being sampled. The user can also view the amplitude spectra, or spectrogram (an amplitude and phase plots) computed upon the average sweep (a sweep is a concatenation of epochs and the average sweep is the result from averaging a plurality of sweeps). When the spectra of the average sweep are displayed, the frequencies of the SS-AEPs or R-AEPs in the EEG data nay be highlighted for easy comparison with background EEG-noise activity (i.e. background noise). The auditory evaluation program 40 also allows the user to view both the numerical and graphical results of statistical analyses that are conducted on the evoked response data to detect the presence of at least one evoked response to a stimulus.

When performing a test which includes single or multiple stimuli, or which includes stimuli whose parameters are sequentially changed, for example, which are presented at two. or more different intensity levels, then the resulting data must be meaningfully organized. In one embodiment, the auditory evaluation program 40 can use the analysis module 46 to organize the evoked response data into a data set so that this data can be analyzed intelligently. The data set my contain data which it organizes into units such as sweeps, accepted data epochs, rejected data epochs, and averaged sweeps, summary results, statistical results, which can be organized based upon the stimuli and intensities tested. The data set may contain many data structures, such as matrices and vectors which may be multidimensional as will be described. The data set enables the auditory evaluation program 40 to efficiently perform signal processing on data needed to obtain the test results.

In one embodiment, the data set is organized into epochs which have been accepted or rejected. The analysis module 46 keeps track of the stimulus parameters which were used to collect each-epoch, and uses this information to form sweeps. The sweeps can be averaged together to form average sweeps, based upon stimulus parameters. For example, if sweeps 1-10 were collected when stimuli were presented at 50 dB SPL, and sweeps 10-25 were collected when stimuli were presented at 40 dB SPL, then two averaged sweeps can be created from sweeps 1-10, and sweeps 10-25, respectively. The sweeps can also be conceptualized, organized, and indexed according to epochs. For example, if 16 epochs are included in each sweep, then the data in sweeps 1-10 can organized and indexed by the analysis module 46 as a data set which includes 16 columns of data and 10 rows of data. The analysis module 46 dynamically organizes the data matrix into sweeps, based upon the status of epochs as accepted or rejected, which may change as a test progresses. When multiple stimuli are used, separate sweeps and separate average sweeps may be created for each stimuli to be evaluated, even when these multiple stimuli are presented at a single intensity. Further, the analyses module 46 may re-organize the evoked response data into numerous additional computational matrices in order to efficiently and rapidly create the sweeps and averaged sweeps needed to analyze the evoked response data and produce summary results for a test. Programming languages such as MATLAB provide data "structures" within which manipulation, storage, and organization of matrix data is handled easily. For example, "cell arrays" enable a matrix to be created, where each cell is a vector or matrix. Accordingly, a 2-by-2 cell array "A" can be created where, $A(1,1)=\{[\text{'all accepted epochs'}]\}$; $A(1,2)=\{\text{'all rejected epochs'}\}$; $A(2,1)=\{\text{'individual sweeps for 50 dB SPL}\}$; $A(2,2)=\{\text{' individual sweeps for 50 dB SPL }\}$. In the cell 1,1 of the cell array, the 'all accepted epochs' data is a matrix where each row is an epoch, and each column the values of the evoked response data at different moments in time. Because cell arrays may be "nested", cell $A(2,2)$ can be a matrix which contains the individual sweeps for 50 dB where all evoked responses are evaluated with the same data (or the same data can be indexed in an n by 16 cell array, where n=number sweeps, and 16 epochs per sweep are stored in 16 columns of the cell array), or can be a (1,4) cell where each cell corresponds to 50 dB SPL sweep data for each of 4 evoked responses being evaluated. Matlab could also manage and index the data using multi-dimensional arrays, matrices, & pages. Further, just as the analysis module 46 can analyze and organize the data matrix so that it analyzes data obtained at different intensity levels separately, it can also analyze the data (and any measures derived from these matrices) which was collected when different stimulus parameters were in effect, to estimate thresholds. The analysis module 46 can analyze the summary results obtained for all the different stimuli and stimulus parameters used during a test to produce test results, using, various techniques such as regression.

The auditory evaluation program 40 has options for collecting and displaying data appropriate for the test protocol. For example, as is commonly incorporated into clinical audiometric devices, the parameters for several clinical protocols can be stored in several parameter files to enable several tests to be run automatically, for example, each with several stimulus intensities or different stimuli. The test results obtained from using different stimuli and different stimulus intensity levels can be displayed in several Test Summary screens where the test results of the patient 60 are presented, for example, in traditional audiogram format.

FIG. 1*b* illustrates the general steps undertaken by the objective audiometric test system 10. The objective audiometric test system 10 first generates a test signal in step M1 which is appropriate for testing an aspect of the auditory system of the patient 60. The test signal may comprise a wide variety of signals including amplitude modulated noise, click train stimuli, ramped signals, and the like. The next step M2 is to transduce the test signal to create an acoustic stimulus and present this stimulus while simultaneously recording the EEG data at step M3. The presentation of the stimulus and the acquisition of the EEG data should be synchronized to accurately represent signals of interest. The next step M4 comprises signal processing and analyzing the recorded EEG data to determine whether there are any responses present in the EEG data or if certain criteria have been met so that further data acquisition is not necessary and the auditory test, or some portion of the auditory test, may halt. This step may also include estimating an auditory threshold based upon responses in the EEG data from the patient 60. Step M4 will typically involve performing a noise reduction method on the EEG data to produce data which has less noise and which is. more homogenous in its characteristics (termed "noise reduced data") and then applying a detection method to the noise reduced data. In the next step M5, Test Results are reported. The steps outlined in FIG. 1*b* may be part of a larger audiometric test battery that will involve iteratively performing each of the steps several times and at different intensities or with different stimulus parameters. These particular audiometric tests and the steps which are involved are discussed in more detail below.

Summary results include from the process of FIG. 1*b*, for all stimuli tested, and for each intensity level or ramping function tested, information concerning the amplitude, phase, statistical probability of the presence of an evoked response (likelihood a sound was heard), confidence limits, noise level estimates, and other measures that may be derived from the data. The Summary Results can be included within the Test Results, however, the test results also include the overall results of the test. For example, the summary results may indicate that the probability of the presence of a response was 0.01 at 50 dB, and 0.29 at 40 dB. The test results will use this to, for example, provide a PASS/FAIL result, or to state threshold for the stimulus is 50 dB. Further, by means of regression, or by subtracting a constant, the Test Results may indicate that the threshold for the stimulus is 40 dB. Accordingly, the Test Results include information which provides the clinician with meaningful audiometric results.

SS-AEP/R-AEP Detection

The EEG data that is sensed during the presentation of multiple SS-AEP and R-AEP stimuli may contain several superimposed responses (as in the case of binaural or multiple-stimulus testing) as well as other EEG activity which is regarded as background EEG-noise (which is estimated in the background EEG-noise level). Due both to the small size of the responses and the superimposition of several responses when using multiple-stimuli, it is difficult to distinguish the SS-AEP/R-AEP responses in the time domain. However, if the EEG data is converted into the frequency domain, using, for example, a Fast Fourier Transform ("FFT"), and the amplitude and phase of each evoked response can be measured reliably at the specific frequency of each modulation/repetition rate in the stimulus.

The SNRs of the SS-AEPs and R-AEPs are very small compared to the background EEG. Accordingly, a sufficient amount of EEG data must be collected in order to increase the size of the response data sufficiently to be recognized as either stable (e.g. phase coherence statistics), or statistically different from background EEG-noise levels (e.g., F-ratio). Conventional approaches to increase the SNR of the evoked response data include artifact rejection and time averaging. Although there are advanced signal processing techniques which offer advantages over simple artifact rejection based upon a fixed voltage level of the EEG signal (some of which are described below), this type of conventional approach can be implemented by the noise reduction module 48, in part because these techniques are still fairly popular with clinicians and research scientists in the field of audiology. Artifacts may introduce large noise spikes that are due to non-cerebral potentials such as movement of facial muscles or the like, and this energy can decrease the detection of responses when not rejected.

Artifact rejection may occur for any epoch of EEG data that is acquired during SS-AEP and R-AEP testing. In SS-AEP recording, if an epoch is rejected, the next epoch that does not exceed the artifact rejection criteria is concatenated to the last acceptable epoch. This concatenation procedure does not produce discontinuities in the data which are of any concern because each stimulus which evokes the SS-AEPs is constructed so that each epoch contains an integer number of periods of the evoked steady-state responses (John and Picton, 2000). The noise reduction module 48 can also perform other types of noise reduction techniques such as weighted averaging, data substitution, data management tasks, etc. The last two techniques may be required to ensure that the recorded EEG data epochs whch are accepted comply with homogeneity criteria (see section entitled Data Quality Control Techniques). The objective audiometric test system 10 contains the noise reduction module 48 which may be adapted to employ artifact rejection in which epochs are rejected based on specific criteria such as an amount of high frequency (e.g., 70-200 Hz) activity. The noise reduction module 48 may further employ other types of weighted averaging as previously described by the inventor (John et al., 2001, PCT/CA 01/00715). As will be described later, artifact rejection and noise weighting are more complicated for R-AEPs because a parameter of the stimulus, such as the intensity of the stimulus, is constantly changing. Accordingly, if an epoch is rejected, the subsequent epoch can not take its place because this epoch contains R-AEPs elicited by acoustic stimuli with a different range of intensities.

As has been described by the Inventor (John and Picton, 2000), time averaging comprises concatenating epochs to form sweeps. A plurality of sweeps are then averaged in time to yield an-average sweep. Time averaging reduces the level of background EEG-noise activity that is not time-locked to the stimuli. As each average sweep is obtained, it is converted into the frequency domain, or time-frequency domain, by the signal analysis module 46, for example, via an FFT, short time Fourier Transform (STFT), wavelet analysis, filtering, adaptive filtering, independent component analysis, or other time-domain to frequency-domain, or time-domain to time-frequency domain, conversion procedure. When converting data into the frequency domain using methods such as the FFT, the sweep duration is an issue since increasing the sweep duration distributes the background noise power across more FFT bins. Thus, increasing the duration of the sweep increases the frequency-resolution of the FFT. The specific frequencies available from the FFT are integer multiples of the resolution of the FFT which is $1/(Nt)$, where N is the number of data points and t is the sampling rate. One possible implementation uses a sampling rate of 1000 Hz, an epoch length of 1024 points and sweeps that are 16 epochs long (16,384 points). Accordingly, the resulting frequency resolution is 0.61 Hz ($1/(16*1.024*0.001)$) and the frequency region in the FFT spans DC (0 Hz) to 500 Hz. Alternatively, sweeps may also be other durations, such as 1, 8 or 12 epochs.

The detection module 50 may provide an EEG-noise level estimate which can be derived from data at neighboring frequencies in the amplitude spectrum. Neighboring frequencies are close in frequency to a response frequency but no SS-AEP occurs in the neighboring frequencies. If there were no SS-AEP in the recorded data then the energy in the FFT which occurred at the modulation frequency, where the response should occur, would be statistically similar to the average noise power across the neighboring frequencies. An F-ratio may be used to estimate the probability that the amplitude at the modulation frequency in the resulting FFT is not statistically different from the EEG-noise level estimate. When this probability is less than 0.05 (i.e. $p<0.05$), the SS-AEP response may be considered significantly different from noise, and the patient 60 is considered to have heard the SS-AEP stimulus. A more stringent criteria, such as $p<0.01$ can also be chosen. The objective audiometric test system 10 can provide a probability for each SS-AEP response based upon the statistics such as F-Ratio and phase coherence. In the case of R-AEP responses, these types of statistics can be applied to spectrogram data which is generated from the signal analysis module 46, using techniques which will be described.

Referring now to the detection module 50, a phase weighted t-test may be used to detect the presence of SS-AEP responses in the recorded EEG data (Picton et al 2001, PCT/CA 01/00715). The phase weighted t-test employs data biasing to detect the SS-AEP response based on a priori knowledge about the SS-AEP response. As described in the prior art, several approaches can be used to define the expected phase. First and foremost, the database 52 contains normative or "expected" phase values. Other methods are also described for choosing correct reference phase values. The detection module 50 may be adapted to perform other statistical methods for detection, such as the MRC method. The use of an expected phase angle has been incorporated as a variant of the Rayleigh test for circular uniformity (RC) termed the modified Rayleigh test (MRC). The RC method can be made more statistically powerful if an expected phase angle is known. Probabilities for these two types of tests are computed using critical values available in standard statistical reference materials (e.g. Zar, 1999).

Audiometric Test Methods

Several novel tests and related methods will be described, all of which offer advantages over the known art. The first tests describe Rapid SS-AEP Screening Tests. The second tests are for rapid screening using the Conditional MASTER Screening Test, which provides some frequency-specific information. The third tests are for rapid screening using the Single-Modulation-Frequency Test, which also provides some frequency specific information. The fourth tests are for obtaining R-AEPs and utilize ramping stimuli to carry out Ramping Stimuli Techniques for Screening and Threshold Tests. A number of embodiments of the Ramping Stimuli Techniques are described such as the Dynamic Iterative Ramping Test, and the Fractionated Iterative Ramping Test, each of which offer advantages not found in the prior art. The fifth type of tests can be used to build a modulation transfer function of the auditory system and detect best modulation rates using Modulation Optimization Tests (MOT). The sixth type of tests evaluate some of the processing abilities of the auditory system using the R-AEP Fine-Structure Tests and the RAMPER Masking Tests. Each of these tests can be realized in a software module which resides within the auditory evaluation program 40.

Rapid SS-AEP Screening Tests

Figure 2:
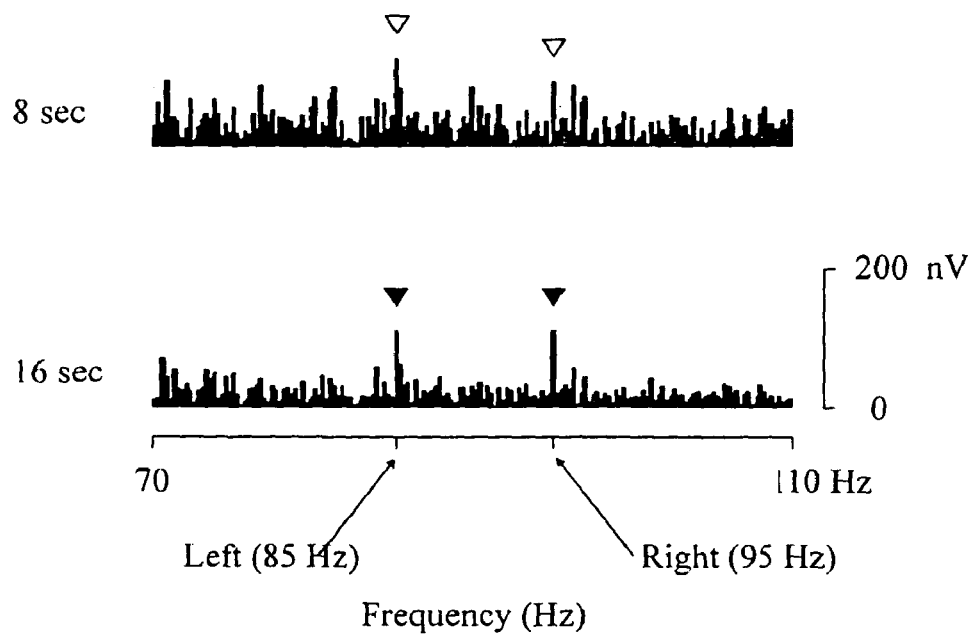
FIG. 2 shows amplitude spectra after 8 and 16 seconds of recording in which two components in the spectra that are at the frequency of modulation of the periodic acoustic stimulus are shown.

In one preferred embodiment, an SS-AEP rapid screening test is accomplished by recording the SS-AEP to at least one amplitude modulated noise (e.g., white noise with band-pass 1-8 kHz) stimulus which is presented to at least one ear of a patient. The inventor has discovered that noise stimuli reliably and rapidly evoke significant SS-AEPs in both infants and adults, which are considerably more robust than the modulated tonal stimuli normally used in frequency specific auditory tests (John et al., 2003a). For example, the experimental results of FIG. 2 provide evidence that this increase in amplitude enables the rapid detection times required in screening tests. Since the filing of the provisional application on which this application claims priority, the inventor has been able to test low intensity stimuli, and show in a group of young infants, that this method works well as a screening test (John et. al, 2003b). Repetition/modulation rates should be chosen to create large SS-AEPs that can be more easily detected in the frequency domain. For adults, the repetition/modulation rates preferably should be above approximately 20 Hz and usually less than approximately 300 Hz, while for infants, the repetition/modulation rates preferably should be above approximately 70 Hz and also less than approximately 300 Hz. The MOT, described later in this application can be used to pick the optimal modulation frequencies to perform screening tests.

FIG. 2 shows data from one adult subject and demonstrates the feasibility of a screening protocol. The responses to the left ear and right ear stimulus appear at 85 and 95 Hz, respectively, which were the rates at which the noise stimuli (1 Hz-8 kHz) were modulated. The stimuli were presented at an intensity of 50 dB SPL, which is about 25 dB above normal hearing threshold. The responses were assessed after 8 seconds and after 16 seconds. The graphs plot a portion of the amplitude spectrum near the frequencies at which the responses appear. Each response (arrowheads) can be considered statistically present at the frequency of stimulus-modulation if the amplitude of the response is statistically larger than the background EEG-noise levels. In this subject, the responses were statistically significantly different from noise at 8 seconds (open arrowheads) and were highly significant and visibly larger than background noise by 16 seconds (filled arrowheads). The fact that these responses were so large, compared to EEG-noise levels, using relatively low stimulus intensity levels, and became significant so quickly was unexpected, and, accordingly, the inventor tested other subjects to see if this effect was reproducible. The inventor was able to elicit these types of robust responses in all subjects that were tested as is shown in FIG. 3.

Figure 3:
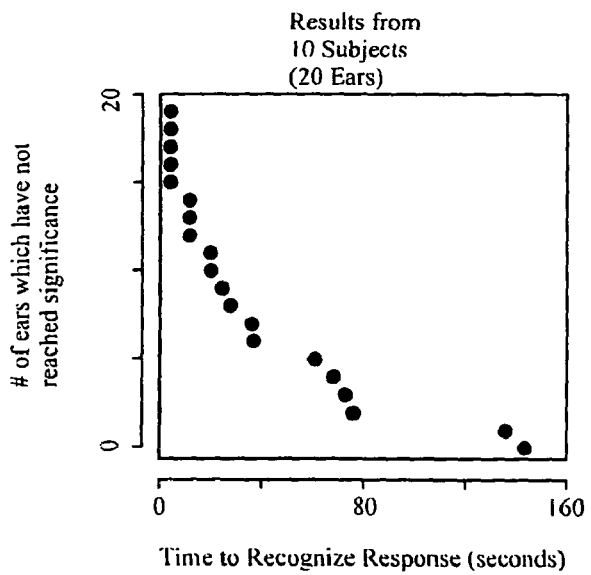
FIG. 3 shows pilot study data showing the amount of time required for responses to reach significance in a test group of 20 ears using an exponentially modulated noise carrier stimulus. The y-axis spans from 0 to 20 and signifies the total number of ears for which the evoked response did not reach significance. By 160 seconds evoked responses had reached significance for all ears.

FIG. 3 shows the distribution of the times required before the responses in 10 subjects (20 ears) were significantly different from EEG-noise level estimates. Seventy-five percent of the responses were significant by one minute, and all were significant before 3 minutes, demonstrating the promise of the procedure as a very rapid screening test. These results have been replicated on other subjects and other types of stimuli have been tested as well. For example, since the time of filing of the provisional application, the inventor has also shown that this technique works well in infants, with 100% of the infants who were tested passing within 43 seconds, using non-conservative statistical criteria and a p-value of 0.05 (John, Brown, Muir, and Picton, 2003b)

The inventor has also demonstrated, using adult subjects, that several novel stimuli may work better than amplitude modulated broadband noise (BBN) stimuli (band-pass 1-Hz to 8 kHz) when used in a rapid screening test. While the response to a BBN stimulus was 77 nV, larger responses were obtained when the modulated noise did not contain lower frequencies. Using a modulated high-pass noise (HPN) stimulus (e.g., 2 kHz to 8 kHz), SS-AEP amplitude increased to 89 nV. Further, the Inventor demonstrated that SS-AEPs can be augmented by simultaneously presenting low frequency sound. When a modulated HPN stimulus was presented simultaneously with a modulated low-pass noise (LPN) stimulus, the response to the HPN stimulus increased to 94 nV. This type of enhanced HPN stimulus is called an EHPN stimulus. Accordingly, BBN, HPN, and EHPN stimuli can all work well for screening. Variations of these stimuli are possible. For example, a different range for the frequencies of the HPN (e.g., 1.5 kHz to 7 kHz) may be used, and the LPN stimulus can be modulated or un-modulated.

The use of amplitude modulated noises for screening is not known perhaps because the size of the responses (and their SNR) at low intensity levels and the resulting rapid time-course needed to become statistically present has never been investigated, and it was not realized that these stimuli could be advantageous in providing a rapid screening test with good specificity and sensitivity. Until the inventor conducted experiments which led to a recent study (John et al, 2003a) it may not have been understood that the response to noise stimuli were of sufficient magnitude to cause the SS-AEPs to become significant within the very short time needed for a screening test. (e.g., within 3 minutes for all the subjects tested). Although the stimuli used in this study were slightly higher in intensity than might be used in a screening test, the data indicated that presenting these stimuli at slightly lower intensities would still enable a screening test to be clinically useful. The average amount of time for most of the responses to become significant was between 30 and 60 seconds for different stimuli tested, with the maximum time being no longer than 2 minutes, and no tested subjects with normal hearing failed to produce a significant response.

Rather than using modulated steady-state stimuli, transient stimuli presented at rapid rates can also produce SS-AEPs. However, in order for the frequency analysis, and other aspects of data processing, to work accurately and efficiently, the transient stimuli should occur at intervals that are equal to integer sub-multiples of the DA and AD buffers. When both ears are tested at the same time, the repetition rate for one ear also should occur at a different rate than that used in the other ear. An example of this method is as follows. The number of points in the DA buffer is made equal to the product of the integer numbers of cycles of the two stimuli within a single epoch multiplied by a power of 2 (in order to produce approximately the same number of points as the DA rate, e.g. 32,000 data points, so that epochs are about 1 second each). A further proviso, that the AD buffer is a sub-multiple, e.g., 1/32, of the DA buffer. This is ensured by choosing the two rates so that the final number of AD-buffer points is divisible without remainder by the number of DA-buffer points (i.e., in this case divisible by 32). For example, the two modulation rates can be 90 and 96 cycles-per-epoch which will result in a product of 8640. This value is then multiplied by 4 to give 34,560 points. This result is then divided by 32, without a remainder, in order to obtain the number of points (1080) that are in each AD buffer. Because the A/D rate is set at 1000 Hz and the AID buffer contains 1080 points, the epoch duration is 1080 ms and the actual frequencies for the two stimuli are 83.33 Hz [i.e., 90*(1000/1080))] and 88.89 Hz, respectively. Both the A/D rate of 1000 Hz and the D/A rate of 32,000 Hz are acceptable since these are both integer submultiples of the clock (e.g., a 20 MHz clock), used by the data acquisition board of the data acquisition system 14.

The inventor recently tested several types of stimuli, which were adjusted to have approximately the same intensity relative to a subject's behavioral threshold (i.e. nHL). The first stimulus was the BBN stimulus. The next two stimuli were condensation clicks (CC) and rarefaction clicks (RC), lasting 125 μs. The remaining stimuli were 1 ms tone-bursts with instantaneous rise and fall times. These bursts contained BBN or a tone (e.g. 1400 Hz). The average response amplitude for the BBN stimulus was 90 nV, for the CC stimulus was 129 nV and for the RC stimulus was 137 nV. The burst-BBN and burst-tone stimuli produced response of 126 and 149 nV, respectively. All of these transient stimuli can be used in rapid hearing screening tests.

When used as a screening test, the stimuli are presented (to one or both ears) at a single level and the subject receives a pass/fail result depending upon whether the responses are statistically determined to be present. Alternatively, the stimuli can be sequentially presented at 2 or more levels. The lowest level at which a response occurs for a particular ear is the threshold for that subject in that ear. The test may be repeated 2 or 3 times in order to ensure the reliability of the results. Additionally, since the overall amount of background EEG-noise will affect the SNR level, and accordingly, response detection, a EEG noise-level criteria can be imposed where the test continues until the amount of background noise is below a specified level. The EEG noise-level criteria can be based upon normative population values and stored in a database.

In an alternative embodiment, because an SS-AEP stimulus presented at 65 dB SPL should become significant almost immediately, a method of performing a screening test can be done at two or more intensity levels whereby the SS-AEP stimulus is first tested briefly, e.g, 10-30 seconds, at a high intensity level, e.g., 65 dB SPL, prior to testing at normal screening intensity levels, e.g., 45, dB SPL. If the individual fails the higher intensity level, then an immediate Fail result is issued, as long as the EEG-noise levels are below a specified level which can be obtained from the database, without spending 1-5 minutes testing at the normal screening intensity level.

If there is too much background EEG-noise in the recorded data, a subject may not show significant responses even though hearing is normal. One method of determining the acceptable amount of background EEG-noise ("noise level criteria") is to use normative data (either a self norm or population norm or combination of the two), whereby the noise estimate must be below a specified value in order for the test to be regarded as valid. Noise level criteria may be obtained from the database 52 and can be applied to all the auditory tests described herein. The EEG noise-level criteria can vary with test protocol and stimulus characteristics (e.g., intensity of the stimuli being tested), characteristics of the noise estimate (e.g., band pass of frequencies used by the estimate), and may vary with test protocol. A method of generating a self-norm for EEG-noise level criteria is to use an early sample of the response data, or data from a previous recording which may have been made using a different stimulus in order to determine what the EEG-noise level criteria should be for that subject. Only if the EEG-noise level estimate reaches one or more of the specified noise-level criteria is the test deemed to be acceptable. Accordingly, noise-level criteria can be used in part, or as the sole determinant, to determine whether a screening test (or testing at a specific intensity in the case of a threshold test) should either continue or be halted. When recordings have too much noise, the auditory evaluation program 40 displays a message that the test results are not valid. For example, a warning signal such as, "Too much noise to perform test accurately" can be displayed.

If the energy in the EEG-noise occurs at the same frequency as the SS-AEP or R-AEP being measured, then the test may indicate that the subject can hear a stimulus, even though this is not the case. This can occur when energy in the background EEG noise occurs at, or leaks into, a frequency bin which is used to measure an evoked response. Homogeneity criteria are therefore important in suppressing false positive or "spurious" results (i.e., a evoked response is determined to be statistically present when in fact it does not exist). For example, if the energy in an epoch is statistically different than for all other epochs (i.e., with respect to total energy, energy in a high frequency or low frequency band, or energy in the frequency bin which corresponds to the evoked response) then this would likely not occur physiologically. Accordingly, using homogeneity criteria will decrease spurious responses because these criteria decrease the chance that spectral energy, which is not related to the evoked response, will show up spuriously in the frequency bins used to measure the energy of the evoked responses.

By measuring the amplitude of the EEG-noise levels for each of the epochs that are collected, it is possible to determine if one epoch has a much larger EEG-noise level or has much larger energy over a specified frequency range, or within a single bin of the amplitude spectrum, than the other epochs. Homogeneity criteria may be adjusted based upon the epochs, or a subset of the epochs (e.g., the set of epochs corresponding to the first 2 minutes of data) that are already collected for a subject. Homogeneity criteria can specify that, for example, in order for each epoch to be accepted, a characteristic (e.g., the energy from 1 to 40 Hz) of that epoch must not exceed a criteria (e.g., must not exceed 2 standard deviations above the mean value as calculated from the other epochs of the data set). As new data epochs are collected, it is possible to dynamically update the homogeneity criteria that are used to reject epochs that do not meet these criteria. In other words, as the test progresses and more data are collected the homogeneity criteria may change since the mean and standard deviations of various measures would change. Accordingly, in one embodiment, epochs that were previously accepted, may become rejected, and vice-versa. Homogeneity criteria may also be based upon normative data obtained from the database. For example, the criteria can be based upon data obtained during a previous test, (e.g., at a higher intensity) for that subject (i.e. a self norm). Homogeneity criteria can be adjusted and applied to the evoked response data continuously, at the end of each sweep, in response to certain events which occur during testing (the probability of the presence of one or more responses changes by a large amount very rapidly), in response to a user's request, or periodically. Homogeneity criteria can be applied at the end of an evoked response testing procedure to ensure the integrity of the results.

Homogeneity criteria can also be created for SNR levels, for example, they can rely upon the mean and standard deviations of an SNR estimate based upon the amplitude of an SS-AEP compared to the amplitude of a noise estimate. As is well known to those in the art, because some frequency domain techniques result in spectral estimation which is related to the length of data which are submitted (e.g., FFT), the amount of energy in the bins of an epoch can be analyzed using zero-padding techniques (e.g., a series of zeros corresponding to the amount of data which would exist in 15 epochs of evoked response data are appended to each epoch which is to be evaluated). In the case of adaptive filtering techniques, such as Kalman filtering, this may not be an issue, since an accurate estimate of the signal amplitude can be obtained with very little data.

Determining if the response is statistically present may be approached in several manners. One method is to determine the average amount of time needed for the responses of a typical subject to reach significance (i.e., the test relies upon population normative data for test time). The typical testing duration can then be limited to this time period and at the end of the test, the evoked response data are evaluated. The evoked responses which not have reached significance produce a "fail" test result. Using population normative data, the maximum test duration can be set equal to the amount of time required for some portion, e.g., 95%, of the population to reach significance. This use of a maximum test period thereby limits the duration of a test. Instead of repeatedly testing an evoked response, the use of a maximum test period can be used to test the evoked response only once and avoid statistical issues of multiple comparisons. Further, some evoked responses should not become significant prior to a minimum amount of time. Evoked responses which become significant prior to this time are probably due to noise entering the frequency bin of the evoked response. Accordingly, use of a minimum test period may increase the duration of a test because, even if the evoked responses become significant immediately, use of a minimum test duration requires the test to continue, however there will be less spurious responses.

Alternatively, the probability of the presence of the evoked responses can be evaluated sequentially, after each data sweep is collected ("sequential response testing"), in order to produce a "significance series". A significance series may be generated as follows. As each sweep is collected, the average sweep is evaluated and the significance level of any responses being evaluated is plotted as a function of cumulative sweep number. Because responses can become significant in less than 16 seconds, and because using a 16 second sweep only permits evaluation of the data in 16 second intervals, the sweep can be shortened to contain only 1 or 4 epochs. Accordingly, a data sweep may be 1.024 seconds in length, or may be longer or shorter. Sequential response testing may lead to a shorter test times, than using a fixed duration for the testing procedure, but may lead to an increase in the number of false positives (i.e., spurious responses) because, as the number of statistical tests carried out increases, the chance of finding significant results increases.

Figures 4A, 4B:
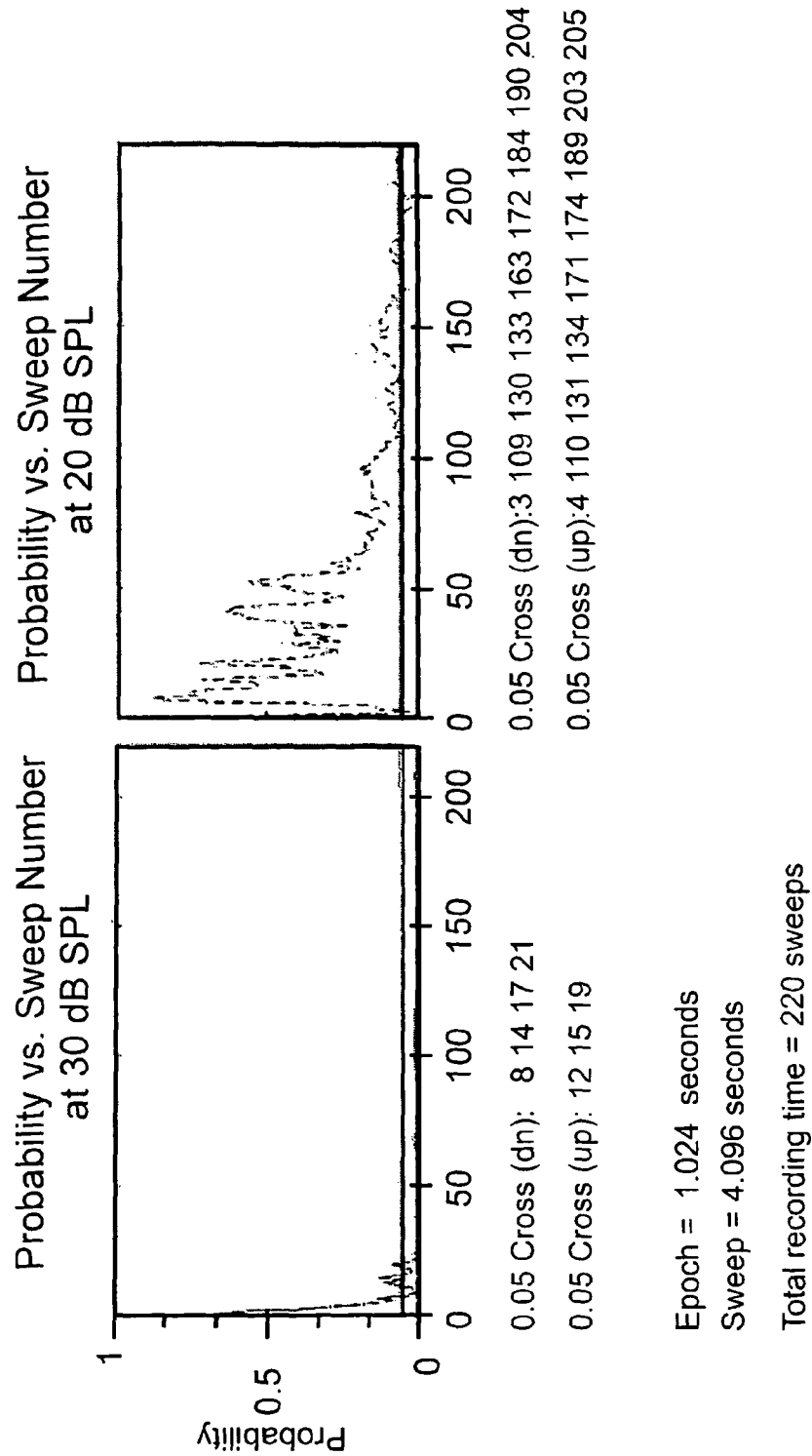
FIG. 4a shows a significance series for responses that was above the subject's hearing threshold, the x-axis is epoch number and the y-axis is probability level.
FIG. 4b shows a significance series for responses that was below the subject's hearing threshold, the x-axis is epoch number and the y-axis is probability level.

FIG. 4a shows an example of sequential response testing of a significance series in a subject presented with two 30 dB SPL modulated BBN stimuli (one to each ear) that were about 5 dB above the subject's behavioral threshold (the SS-AEP to only one of the two stimuli is shown). FIG. 4b shows sequential response testing in a subject presented with 20 dB SPL modulated BBN stimuli that were about 5 dB below the subject's behavioral threshold, and which should therefore not evoke a statistically present response. The data were generated by collecting 220 sweeps of 4-seconds each and evaluating the data (using the F-Ratio) to determine if a response was present at the 0.05 significance level after each sweep was collected. Below each figure is a series of numbers. The upper row contains points where the response transitioned from being non-significant to significant at the 0.05 level (i.e., "0.05 Cross (dN)"). The lower row contains points where the response transitioned from being significant to non-significant at the 0.05 level. For the stimulus which should have been heard, the average data made from iteratively adding the current sweep to a running average sweep, indicates that from 8 to 12, 14 to 15, 17 to 19, and then from 20 onward the response was statistically present at the 0.05 level of significance. In FIG. 4B, the significance series reaches the 0.05 level briefly (for only 1 or 2 sweeps) near the middle of the test period. Later on there are two sections of the significance series where the significance criteria is met for a longer period, such as from 163 to 171, which is a span of 8 sweeps (i.e., about 32 seconds).

Accordingly, while the data in FIG. 4a reach significance quickly (within 21 sweeps or 84 seconds), the data in FIG. 4b also become significant for a limited period towards the end of the recording. If testing was simply halted when the response reached significance then the data in 4b would yield a "false positive" result, suggesting that the subject heard the modulated signal, when in fact this was unlikely. This type of false positive evaluation would be expected to occur due to the use sequential response testing, which relies upon multiple comparisons.

The problem of multiple comparisons can be countered using techniques which incorporate "statistical conditional criteria" (SCC). One technique, termed the "absolute count", uses a SCC in which a specific number of sweeps must reach significance before the response is considered significant. In other words, the response must be evaluated as significant for a specified number of sweeps. Using an absolute count SCC whereby 40 points must be significant would result in the data of FIG. 4b being correctly classified as a "response absent" result (i.e., "Fail"). Another SCC technique, termed the "sequential count", requires that a response must demonstrate significance across a specified number of consecutive sweeps before the response is considered significant. In other words, the response must remain significant for a specified number of sweeps. Using a sequential count criteria whereby a response must remain significant for 5 consecutive sweeps would result in the data of FIG. 4b being classified as a "response absent" result. Another technique, termed the "relative count", requires that the ratio of the number of sweeps that reach significance divided by the number of sweeps that did not reach significance must be above some value before the response is considered significant. Using a relative count criteria whereby 80% of the total number of points must be significant would also result in the data of FIG. 4b being classified as a "response absent" result. The absolute, relative, and sequential count criteria can be applied to the entire significance series, or may be applied to 2 or 3 subsections of the series. Each subsection can continue to analyze an average sweep, or each subsection may contain a significance series which is computed upon average sweep which is based only upon the data which corresponds to the time over which that subsection is being evaluated (i.e. separate significance series are generated for 2 or 3 average sweeps which are created from 2 or 3 sections of the data). The results of the SCC which are applied to each section can be combined to determine whether a response is statistically present.

Several criteria, such as SCC, may be combined. For example, the relative count criteria technique could be combined with a criteria that dictates that a minimum number (e.g., 30) of sweeps (i.e., a minimum test period criteria of about 120 seconds) are required prior to allowing the application of SCC to the significance series. In FIGS. 4a and 4b, significance series and SCC, could have been generated with a 0.01 critical significance value rather than a 0.05 critical significance value. Further, the critical value relied upon does not have to be constant, but can change as the recording period progresses. For example, the critical value could reflect the 0.05 level as it is adjusted using the Bonferroni method, whereby the significance level is decreased to increasing stringent probability levels as more comparisons are made. The SCC values can be obtained from the database 52, for the different test protocols used.

By collecting data on a large normal population for a test protocol, the normative values for absolute count, absolute consecutive count, and relative count can be computed using critical values of 0.05, 0.01, or other critical values so that these SCC yield the desired levels of false positives and false negatives. For example, ROC analysis can be generated as, is well known to those in the art, in order to evaluate the accuracy of using various SCC. The number of false positives can be measured by evaluating frequency bins, which do not correspond to a modulation/repetition rate of a stimulus being tested, and computing how many are statistically present (e.g., counting how many bins are significantly larger than the noise estimate). The number of false negatives can be measured by evaluating frequency bins that correspond to a modulation/repetition rate of a stimulus being tested, and computing how many are statistically absent although they should be present (e.g., counting how many bins fail to be significantly larger than the noise estimate). The appropriate values for various SCC can also be determined using permutation simulations, whereby data from a number of actual subjects is re-sampled in order to create a large number of "virtual subjects", on which the normative values are based. For example, 150 epochs of evoked response data are randomly chosen, from the 220 actual epochs which were collected. This process is repeated 40 times, in order to create 40 virtual subjects. A dataset of 400 subjects can be derived from 40 subjects, and normative values can be derived. This data set can then be subjected to ROC analysis to compute what the SCC should be to obtain a desired level of sensitivity and specificity.

The screening test described here is novel and advantageous over prior art for several reasons. For example, it uses SS-AEP stimuli to perform rapid tests of hearing, which, even at threshold intensities, are shown to provide robust responses that rapidly can be shown to be statistically present in normal hearing. The screening tests can utilize, for example, novel steady-state stimuli, such as EHPN stimuli, to generate SS-AEPs. The screening tests can also utilize specially designed periodic stimuli to generate SS-AEPs. Even though some of the stimuli have some frequency specificity, the main aim of the rapid screening technique is to provide pass/fail result for overall hearing ability. However, an additional aim is to provide a rapid pass/fail result for specific frequency ranges. Two or more stimuli can be presented simultaneously in each ear. The stimuli described here can also be used in a rapid threshold test. The screening test also utilizes novel methods such as the incorporation of a significance series, statistical conditional criteria, and homogeneity criteria. The use of noise-level criteria, homogeneity criteria, maximum and minimum test period criteria, and significance series with SCC are novel methods which can also be applied to many of the testing protocols now described as well as to the MASTER technique of the prior art.

Rapid Screening Using the Conditional MASTER Screening Test

The rapid screening methods already described use various stimuli, that range in their frequency specificity, in order to obtain a quick estimate of an individual's overall hearing ability. Accordingly, while there was a limited frequency range in some of the stimuli described one use of the tests is for non-frequency specific screening or evaluation of non-frequency-specific thresholds. For example, the EHPN stimulus uses two types of band-limited stimuli that are somewhat frequency specific to quickly obtain a simple indication that the auditory system could respond to sound, rather than to specifically screen for frequency-specific hearing loss in those two frequency regions. These methods of rapid SS-AEP screening are therefore similar to the click-evoked ABR test, in that they are not intended to be frequency-specific, but the ASSR test should be faster. Since the rapid ASSR screening tests, and the click-evoked ABR test which is used currently for first stage of screening, are not frequency specific, subjects with good hearing over a limited frequency range, but who have frequency-specific hearing loss, may obtain a "pass" result. However, these types of narrowband or band-limited noise stimuli can also be used, instead of, or in addition to, pure tones, in order to perform a rapid frequency-specific screening test.

By using the MASTER technique to test hearing at both low and high frequencies, Perez-Abalo et al. (2001) suggested that ASSR's could be used as a rapid frequency specific screening test. They used the 500 Hz response and the 2000 Hz response (both stimuli presented at 50 HL) in their "screening" procedure and found that they could perform 'screening' similar to the click-ABR test. The use of noise-level criteria, homogeneity criteria, maximum and minimum test period criteria, and significance series and SCC can be incorporated into their test to improve its performance. Additionally, the Conditional MASTER Screening test, can be used as a rapid frequency-specific screening test which can be faster and more reliable than this prior art. For example, in a Conditional MASTER Screening test, the MASTER test is used with three or more stimuli, and a criteria for passing can be set where, for example, if any specific number, such as any 2 or any 3 of the SS-AEPs, reach significance, then the subject will pass the test. This is an improvement over the prior art because, rather than requiring the 500 and 2000 Hz responses to reach significance, the subject will pass regardless of which 2 (or 3) responses become significant. For example, if either the 500 and 1000, or 1000 and 4000, or other combination of 2 responses (or 3 responses, if that is the pass criteria) becomes significant, the subject will have been deemed to pass the test.

This type of alternative test is a compromise between having a frequency specific threshold test, and a non-frequency-specific test that is currently provided in the click-ABR test. The Conditional MASTER Screening test can be accomplished using either pure tone stimuli, or band-limited noise (including narrow band noise), as the carrier signals. The modulation envelopes effect 100% modulation for the modulated stimulus, and can be modulated at rates of between approximately 30 Hz and 300 Hz. Because the thresholds for different regions of the cochlea may be different, the individually modulated stimuli can each be adjusted to an appropriate intensity prior to being combined into the MASTER stimulus (i.e., the four stimuli can each have different intensities).

The Conditional MASTER Screening tests have some statistical concerns because responses may become significant by chance for a short period of time, due to energy which happens to be in the bins associated with the modulation frequencies, and is merely due to chance. Accordingly, noise-level criteria, homogeneity criteria, maximum and minimum test period criteria, and significance series and SCC can be used. The SCC can be applied across multiple stimuli. For example, in one embodiment, at least a specified number of SS-AEPs must become significant and stay significant, according to a specified critical value of significance such as $p<0.05$, for a specified number of sweeps (specified using sequential count SCC) in order for these responses to be considered statistically present and for a "Pass" result to occur.

In one embodiment, a method of performing a rapid auditory screening test according to Conditional MASTER Screening Test comprises:
a. presenting at least three modulated acoustic stimuli to at least one ear of a subject;
b. recording evoked response data which is organized into data epochs;
c. classifying each of the data epochs into accepted epochs and rejected epochs;
d. processing the accepted epochs to determine which SS-AEPs are statistically present;
e. repeating steps a-d until at least one specified criteria has been met such as a minimum test period criteria, a minimum noise level criteria, all of which can be based upon normative data which is obtained from the normative database; and,
f. providing a pass result if at least a specified number of SS-AEPs were statistically present and a fail result if less than a specified number of SS-AEPs were statistically present.

In this embodiment of the Conditional MASTER Screening Test certain methodology may used. For example, in order to compensate for multiple comparisons, in step d, each SS-AEP is not statistically present until a significance series has been generated for each SS-AEP, and this has successfully passed one or more statistical conditional criteria. In addition to, or as an alternative to using SCC, the specified criteria of step e, can be an amount of time or a level of background EEG-noise present in the recording (i.e., noise-level criteria). The classification of the data in step "c" can be based upon failure or success of the data epoch in meeting homogeneity criteria.

An alternative embodiment of the Conditional MASTER Screening Test comprises:
a. performing a MASTER test with at least three stimuli presented at specified intensities;
b. stopping the MASTER test after a certain amount of time or after a noise-level criteria have been met;
c. providing a pass result if at lease a specified number SS-AEPs are assessed as statistically present.

This embodiment can also utilize homogeneity criteria and statistical conditional criteria Single Modulation Frequency Test An alternative screening test, which provides a compromise between a frequency-specific screening test and a rapid overall test, is the Single Modulation Frequency (SMF) test. In the SMF test, two or more carrier frequency stimuli are modulated at the same rate, in order to produce a larger SS-AEP than would occur when the two carriers were each modulated at their own rates and produced two separate responses. In the SMF test, the failure of the SMF stimulus to reach significance indicates a hearing deficit in one of the frequency specific areas which is being stimulated by the frequency specific stimuli.

The SMF test can also be accomplished using a "virtual SMF stimulus". A virtual SMF stimulus can be created by presenting several carriers, each modulated at a unique modulation rate as occurs during the conventional MASTER test. The responses are then virtually added together, and compared to a noise estimate. In this case, the virtual SMF response can reach significance rapidly, but there is still frequency specific information available. If the SMF response does not quickly become significant, indicating that the subject has not passed the test, then the SMF test is allowed to continue and the responses to each of the MASTER stimuli are evaluated as would occur during a normal MASTER test. Both the SMF and virtual SMF stimulus have been described by the author (John, Dimitrijevic, and Picton, 2003).

In one embodiment, a method of utilizing an SMF test comprises:
a. performing a MASTER test with at least 2 SS-AEP stimuli that are modulated at the same single modulation frequency; and,
b. analyzing the resulting SS-AEP data to determine a pass or fail result.

In another embodiment, a method of utilizing an SMF test comprises:
a. performing a MASTER test with at least 2 SS-AEP stimuli with unique carrier and modulation frequencies;
b. processing the resulting SS-AEP data to derive a virtual SMF response; and,
c. determining if the SMF response is statistically present in order to generate a pass or fail result.

Methods for R-AEP Screening Tests and R-AEP Threshold Tests

Stimuli

In one embodiment, a method is used to achieve rapid estimate of a subject's hearing threshold, whereby ramping evoked potentials, or "R-AEPs", are evoked by a ramping intensity stimulus. Various functions may serve as the ramping envelope. Because intensity is measured upon a log scale, using decibel (dB) units, a ramp which has a linear growth function when plotted in dB units is one of several appropriate ramp functions that can be used. Because any large jump which occurs in the stimulus intensity, or other characteristic of the ramping stimulus, may be startling to a subject, it may be preferable to use a symmetrical ramping function which consists of a first half that increases in intensity, followed by a second half that decreases in intensity. The last part of the stimulus can be presented at an intensity which is equal to that of the first part of a subsequent stimulus so that no discontinuities are experienced by the subject. Symmetrical ramping functions thereby avoid the large changes in stimulus intensity that would exist if a simple continuous increase or decrease of intensity were used. However, either one-sided or symmetrical or non-symmetrical ramp functions can be used.

One method of creating a ramping stimulus, comprises digitally multiplying a ramping function with a base signal. A base signal can be conventional types of modulated, steady-state, or periodic stimuli. Repetition/modulation rates of the base signal should be fast enough to create oscillatory ramping responses that can be evaluated by time-frequency analysis. In adults this should be above approximately 30 Hz and usually less than approximately 300 Hz, while in infants this should be above approximately 70 Hz and less than approximately 300 Hz An example of creating an intensity ramping stimulus is now provided. The base signal, such as an amplitude modulated BBN stimulus, should range between −1 and 1 (depending upon the range of the D/A buffer of the data acquisition card, these values can be in volts or can be in arbitrary units, which are later adjusted to utilize the full range of the card). In a programming language called LabVIEW, the broadband noise can be created with the subroutine called "uniform white noise.vi", which is then modulated at a particular frequency. After the base signal is created it is multiplied with the ramping function in order to create a ramping stimulus. The ramping function preferably ranges between 1 and zero. When the instantaneous value of the ramping function is 1, the ramping stimulus will therefore have its maximum intensity. The maximum intensity is equal to 1, with the decrease in intensity being determined by the equations:

$$I_t = 10^{\wedge}(-t*C)$$

where $I_t$ is the SPL level at a given time-point, "t" is the current time-point and C is a constant that is equivalent to the intensity step with C being defined by $$C = R/(N*20)$$

where R is the desired range of intensity in dB, and N is the number of points in the ramp function. Accordingly, if R is set to 10 and the base signal has an amplitude which will produce an intensity of 50 dB SPL then the ramped stimulus will decrease from 50 to 40 dB SPL. An upward ramp can be generated by taking the original ramp function and reversing the order of the points. By setting N to ½ of the total number points of the desired stimulus length, and then reversing the original function and adding this result to the original function, a ramp stimulus of N length can be created which contains both an upward and downward going ramp (i.e., a symmetrical ramp). Other types of ramping functions can also be used, including linear, non-linear, and multiple slope functions. For example, a ramp can contain two slopes with the first slope being relatively shallow and lasting for 80% of an upward ramp, while the remaining 20% of the upward ramp has a steeper slope. This may be useful since R-AEPs evoked by lower intensity stimuli have a lower SNRs than R-AEPs evoked by higher intensity stimuli. Accordingly, more time is spent obtaining a stable estimate of R-AEPs with lower SNR levels so that these are estimated with a more similar degree of accuracy as the R-AEPs obtained to higher intensity stimuli. A ramping stimulus can also be created by analog means whereby the intensity of a programmable audio amplifier is dynamically adjusted according to the ramping function.

When the R-AEP test involves creating a R-AEP stimulus which varies in intensity, then the ramping function can be multiplied with the base signal as just described. As will be described in other methods disclosed herein, the R-AEP stimulus can change for a different attribute than intensity, such as modulation rate (e.g., ramping from lower to higher modulation rates over time in one case), carrier frequency (e.g., ramping from lower to higher carrier frequencies over time, while holding modulation rate constant in one case), stimulus type (e.g., ramping from a broadband to narrowband carrier signal over time), or for a different feature of the stimulus. The creation of ramping stimuli, which are not intensity ramping stimuli, does not always entail multiplying a base signal with a ramping function, but rather, is accomplished using more complex mathematical equations, where the quality of the stimulus which is to be ramped, changes appropriately with time. For example, the function in MAT- LAB called "chirp" may be used to generate ramping stimuli. The function enables parameters of a stimulus which ramps in instantaneous frequency to be easily set. The function permits the setting of the initial frequency, final frequency, time of ramp, initial phase of ramping frequency, the shape of the ramp (e.g., determines whether the sweep frequencies vary linearly, quadratically, or logarithmically), whether the ramp is positive, negative, or unidirectional/symmetrical (bidirectional), as well as other features of the ramping function. When the ramping stimulus is to ramp across carrier frequency, the output of the chirp function is used to create the carrier signal. When the ramping stimulus is to vary in its modulation rate (e.g., as occurs in the MOT), the output of the chirp function is used to create the modulation function. Alternatively, a standard equation such as $ramp_i = A_i * \sin(2*p_i*f_i*t_i+\Phi_i)$ can be used to create either the carrier or modulation function of a ramping stimulus, where $A_i$= the instantaneous amplitude, $Ramp_i$=the instantaneous value of the ramping stimulus, $f_i$=instantaneous frequency, $t_i$=the time, and is the instantaneous phase of the stimulus. Some methods of creating modulated stimuli have been described by the inventor (John & Picton, 2000). Like the ramping intensity stimulus, because the attribute of the stimulus which is being ramped will have specific values at any moment in time, using time-frequency analysis of the R-AEP data enables the evaluation of the response to the stimulus at any given point in time.

General Method

Figure 5:
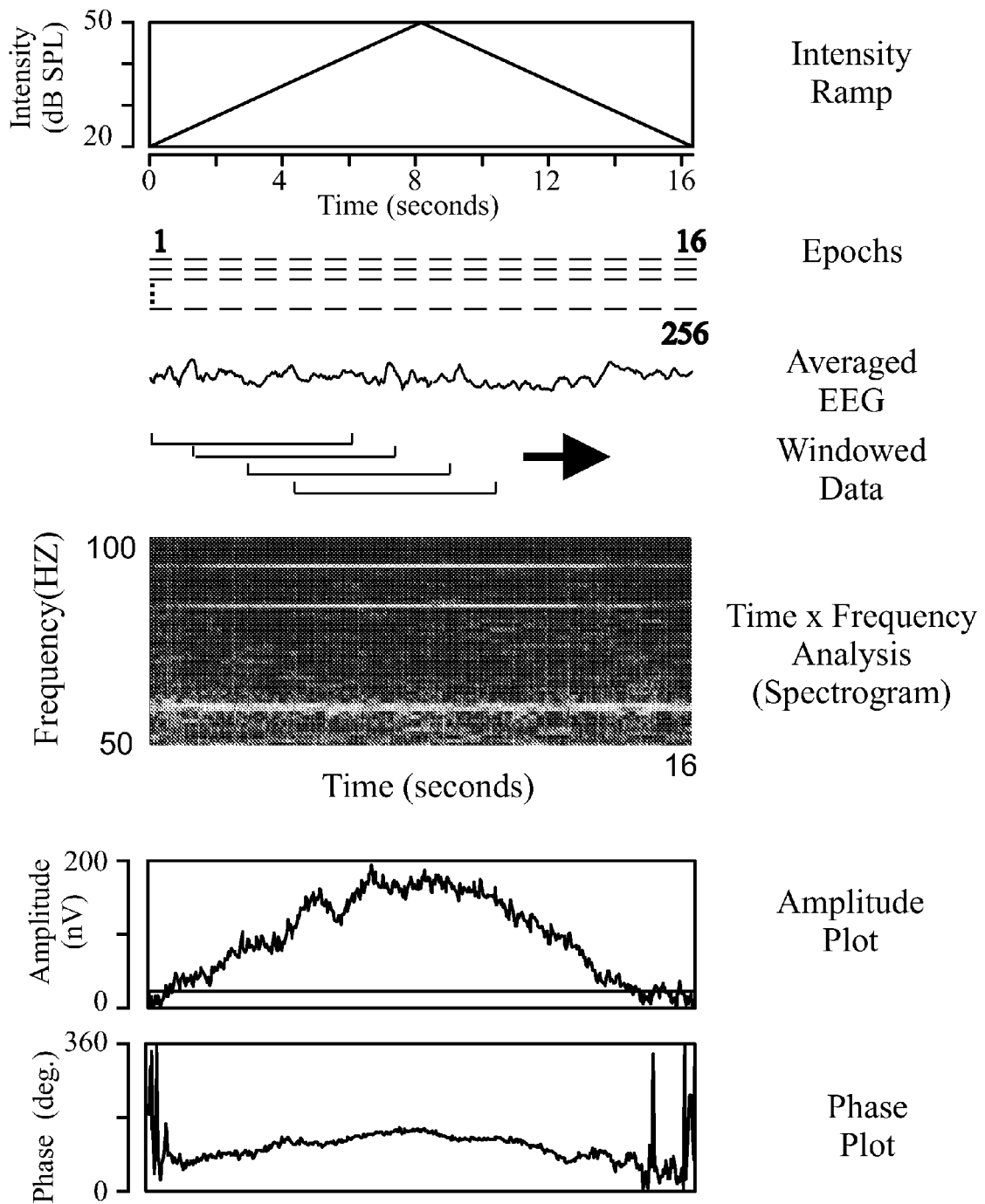
FIG. 5 is a series of plots that illustrate a procedure for generating a spectrogram and amplitude and phase plots using data from 1 subject.

An example of performing a ramped intensity test is shown in FIG. 5, and is reflective of what the Inventor has used in some initial studies with the method. The first panel of the figure shows the intensity of the ramp stimulus, which increased from 20 to 50 db SPL during the first ½ of the data sweep (8.192 seconds) and then decreased for the second half. This is a symmetrical ramp stimulus. As can be seen in the second figure panel, the recorded EEG data were stored in 256 epochs (16 sweeps of 16 epochs each), lasting 1.024 seconds each. The contiguous epochs were concatenated into 16.384 sec. sweeps which are shown as rows in the figure panel and were averaged together in the time domain (each column is averaged together). In this example, 16 sweeps were collected, causing the recording to last about 4 minutes. The third figure panel, shows the resulting 16.384 sec. averaged sweep, which will contain responses that occurred over the entire range of the ramping stimulus. Accordingly, while the evoked response data are still collected in data epochs, the ramping stimulus spans across the entire sweep.

The averaged sweep may be analyzed in several manners in order to obtain the time-frequency information. For example, a spectrogram can be created by using a moving window of, for example, 1024 points, with an overlap of 1000 points (i.e., the window is iteratively shifted through the data by 24 points). The entire 16,384 point waveform can be analyzed in 682 (16384/24) separate FFT's which will yield a spectrogram. Such a spectrogram is shown in the next panel of FIG. 5. The responses to stimuli presented at 85 Hz (left ear) and 95 Hz (right ear) can be seen as 2 horizontal lines towards the top of the spectrogram which are distinctly larger than the background noise (the larger the amplitude, the lighter the color on the plot). A fuzzy line also appears at 60 Hz due to line noise in the measurement environment. By extracting the row equivalent to the frequency of the modulated stimulus (or repetition rate if transient stimuli are used), one obtains the amplitude and phase of the response over time. The amplitude and phase plots of the responses to stimuli presented to the left ear (85 Hz) can be seen, as a function of time, in the next two panels of FIG. 5. As the intensity of the ramp is increased, the amplitude of the response increases and the phase values stabilize rather than being random.

The R-AEPs can be statistically evaluated to determine if a response is present by comparing the R-AEP amplitude, at any moment in time, to a noise estimate. For example, by extracting amplitude values of the rows (i.e. neighboring frequencies) of the spectrogram which are adjacent to row of the spectrogram for the frequency of modulation for the R-AEP stimulus (or the repetition rate for transient R-AEP stimuli), an estimate of the background EEG-noise (over time) can be obtained. This estimate of background EEG-noise can be used in order to carry out an F test. In this illustrative example, 10 rows above and below the rows corresponding to the frequencies of modulation (for the multiple ramping stimuli) are used in the noise estimate, and the R-AEP estimates, at different moments of time, are compared to the noise-estimate using an F-test with 2 and 19 degrees of freedom. In this example, the amplitudes (and phases) of the R-AEPs at different moments in time are compared to an EEG-noise estimate which was equal to the average EEG-Noise across the whole sweep (i.e., the amplitudes of the noise were collapsed across time). Alternatively, the EEG-noise estimates at different moments in time can be used in the calculation of the F-statistic. Similar to the MASTER technique, when generating the EEG-noise estimate, the rows corresponding to the frequencies of the other R-AEP stimuli are skipped. In the amplitude plot shown in FIG. 5, both the amplitude of the R-AEP over time and the average level of background noise (across the entire averaged sweep) are shown.

In order to estimate intensity thresholds for the ramping stimuli presented to the subject, the information in the amplitude plot, phase plot, or a mixture of the two types of information can be used, as is known in the art. The estimation of threshold can be based upon the raw data, or can be obtained using regression. If a threshold is estimated from the raw data then threshold can be defined as the point at which the amplitude of the R-AEP is not significantly different than the EEG-noise estimate. Since the intensity of the ramped stimulus is known at every point in time, it is simple to calculate what the intensity of the intensity ramped stimulus was when the R-AEP failed to be significant. For example, if the R-AEPs begin to be statistically present at 4 seconds, then the threshold can be calculated to be about 35 dB SPL (the slope of the intensity function in first panel of FIG. 5 is 30 dB range over 8 sec or 3.75 dB/sec). Since there is a 1 second window, the range for that data is 35+/−1.875 dB. Accordingly, the threshold can be estimated as between about 27 and 32 dB SPL. Alternatively, if physiological threshold is thought to occur at 10 dB above behavioral threshold, then the threshold could be calculated, incorporating this correction factor, as 17 to 22 dB SPL. As in a MASTER test, the correction factors can be specified for different carrier frequencies, ages, and stimuli.

Smoothing of the amplitude or phase plots may occur prior to estimation of threshold. Other types of signal processing can be used upon the amplitude and phase plots, or on the actual spectrogram as well. For example, an estimate of a patient's threshold for a ramping stimulus can be based upon the lowest intensity for which the R-AEP amplitudes are not statistically different than an EEG-noise level estimate, or can be based upon the lowest intensity for which the R-AEP phases are not statistically stable, may utilize regression techniques which can be applied only to R-AEP amplitudes (which are statistically present) or phases (which are statistically stable), and the regression techniques can applied only to R-AEP amplitudes which occurred in over a limited time period or intensity range of the stimulus. For example, using regression, only data obtained when the ramping stimulus is in the higher intensity range can be used in the estimate of threshold. As is known to those skilled in the art, the epoch length, the sweep length, the size of the moving window, and the number of points in the overlap can be changed without significantly deviating from the methods described in this patent specification.

Symmetrical ramp stimuli can provide 2 estimates of threshold, based upon the data from the upward ramp and the data from the downward ramp. Alternatively, since the data are symmetrical around the maximum of the ramp, the amplitude and phase data from the second half of the test can be re-sorted in reverse, and added to the data obtained for the upward ramp to obtain mean values. If the ramping responses evoked by the downward ramp were different than those obtained to the upward slope due to, for example, louder stimuli being presented just prior to a softer stimuli (e.g., as may occur due to masking or hysteresis) then the first and second halves of the ramping results would be different, but initial work by the inventor has not found this to be the case. Computing the mean amplitude from the first and second halves of the data gives a more reliable estimate of amplitude at a given intensity, but would not act to reduce the overall level of the EEG-noise floor. By obtaining the mean of the complex spectra from two data windows rather than merely the two amplitude values, better estimates can be obtained for both the signal and noise bins since the phases of the energy are taken into account. In order to average the complex spectra, the data window should start at the same time for epochs on both sides of the ramp. This can be done by using integer sub-multiple of the epoch length (e.g., in 1024 point epoch, the data windows must be advanced by either 32, 64, 128, etc time-points). Otherwise only real rather than complex values are used for estimating amplitude. For phase data this stipulation is not really necessary because combining phase from slightly different areas may only slightly affect calculations of phase stability or "coherence".

The data in FIG. 5 can be analyzed in several ways in order to determine the frequency-specific hearing thresholds of a subject. For example, only significant points of the time-frequency data can be used (i.e., R-AEP amplitude values whose squared values are larger than the sum of the squares of the EEG-noise estimates are considered significant) to estimate threshold. A regression line can be fit to R-AEP amplitudes that correspond to the significant points of the ascending slope of the R-AEP amplitudes. The intensity of the ramping stimulus (which corresponds to the values of the x-axis) at the point where the regression line intersects the x-axis is taken to be the behavioral threshold. Additionally, when a symmetrical ramping stimulus is used, a second regression line can be fit to amplitude values that correspond to the significant points of the descending slope of the response function. A combination (e.g., the average) of the x-intercepts for the regression lines fit rising and falling functions can then be used as an estimate of threshold. Alternatively, the upward and downward R-AEP data can be combined, and the result can be used to estimate the x-intercept and thereby estimate threshold.

Alternatively, rather than using an amplitude criteria that compares signal-to-noise, the R-AEP amplitudes that are used to fit the regression lines can be selected based upon criteria that are based upon the R-AEP phase data (e.g., slope of the phase or phase variance). For example, only R-AEP amplitudes having a distribution of phase values which suggest that a R-AEP is statistically present can be used to calculate threshold. Alternatively, the amplitude and phase data can both be used to select the spectrogram data (i.e. amplitude and phase values of the R-AEPs) that should be used to calculate threshold (which may occur through regression). For example, only ranges of amplitude and phase data which indicate that an evoked response is statistically present are used in a procedure which utilizes both amplitude and phase information to estimate threshold.

When using FFT based techniques, or other techniques which analyze the data by sequentially windowing sections of the data, the phase data of the spectrogram may be defined arbitrarily, in relation to the beginning of the current data window, rather than being defined in relation to the phase of the stimulus. While the phase of each ramping stimulus is invariant, for example, zero at the beginning of the recorded epoch, the phase of the evoked response, as evaluated in each data window, is a function both of the point in time of the beginning of the data window and the modulation rate of each ramping stimulus. The phase data should therefore be re-defined in relation to some common reference in order to be meaningful. The actual phase, in relation to the beginning of the x-axis of the spectrogram, can be computed by adding the phase data of the spectrogram to phase values that are related to the offset of the window from the beginning of the spectrogram using the equation:

$$\theta_a = \theta_c ((T_c/L)^* 360$$

where $\theta_a$ is the actual phase value of the response frequency being measured, $\theta_c$ is the current phase value of the current data window in the spectrogram, $T_c$ is cumulative time for the total number of points that have occurred in the response data from the beginning of the recording and prior to the first point of the current window in the spectrogram, and L is the cycle length of the modulation frequency, or the duration of the inter-stimulus interval (both cycle length and inter-stimulus interval can be referred to as the "stimulus period"), of the at least one ramping stimulus that was presented to the subject.

Data Quality Control Techniques

The use of a spectrogram to look at time-varying spectral data is known in the art. However, certain rules should be followed when using ramp stimuli tests. Because the time series data is time-locked to a continuous stimulus, ramping stimulus methods may fail or severely under-perform when certain methods are not incorporated into the analysis of the data. The following methods, such as applying homogeneity criteria, the zero replacement technique, the swapping replacement technique, and the repeating replacement technique, are novel from, and offer advantage over, the prior art. Data Quality Control Techniques ensure that the data which are analyzed are of the high quality leading to increased accuracy of threshold estimation or other type of audiometric evaluation. These techniques include applying homogeneity criteria, but this is more difficult for a ramping test than for an SS-AEP test. As can be seen in FIG. 5, the columns epochs within the sweeps are locked to a particular attribute, in this case intensity range, of the ramping stimulus. All the epochs in the first column will have evoked responses which where elicited by the lowest intensity stimuli, the second column contains data evoked by a higher intensity, and so forth. In conventional steady-state recording techniques an epoch may be rejected if the EEG-noise level is above some threshold value, and a subsequent epoch can be used in its place. However, if this is done in the ramping technique, then the columns of the data matrix (i.e., the epochs in the individual sweeps) will contain R-AEPs elicited by stimuli of many different intensity ranges, (or other characteristic of the stimulus which is ramped) and will not be sensible. Weighted averaging can be used instead of artifact rejection somewhat successfully. However, if there is a large amount of EEG-noise within an epoch, then when the epoch is multiplied by the weighting factor, the estimate of the signal will also be diminished.

Several techniques can be used with ramped stimuli to reject epochs which have too much noise or which do not meet criteria, such as homogeneity criteria. In the zero replacement technique, a noisy epoch is replaced with zeros so that the averaged sweep is not affected by that epoch, and the average of the column of data (e.g., epoch #2 within each sweep) is divided by n−1 rather than n, where n is the number of total sweeps collected. In the swapping replacement technique, the epoch with noise is replaced by an epoch from a different sweep which is in the same column. In the repeating replacement technique, the epoch with noise is replaced by an epoch which is collected while a section of the ramping stimulus which corresponds to the epoch which was rejected, is repeated an extra time, for example, during the next iteration/repetition of the ramping stimulus.

Epochs can be rejected using several criteria. Simple threshold criteria can be used and can reject epochs based upon the absolute amplitudes of the time series data or the amount of acceptable high frequency energy within in an epoch (e.g., spectral energy from 70 to 200 Hz). However, because the slope of R-AEP responses over time is used to determine threshold, using homogeneity criteria, rather than simple threshold-criteria may ensure that the data can be optimally evaluated. An example of homogeneity criteria is an inter-epoch noise criteria, wherein the amount of noise in any given epoch can not be more than, for example, 200% of the average amount of noise measured in other epochs of that sweep. Alternatively, the inter-epoch noise criteria may be applied across sweeps, where as more data is collected, the average level of noise for that subject becomes more stable. Inter-epoch noise criteria may be used both within sweeps, across sweeps, or both. Inter-sweep noise criteria may also be used, where an entire sweep is rejected if it has substantially more noise than the other sweeps.

Homogeneity criteria are more useful than merely rejecting an epoch of data because it has more noise than a cutoff value defined based upon normative data. For example, while a "quiet" subject may produce data that is well below a threshold criteria that is set based upon population normative values, the intra-subject noise may still vary considerably (e.g., due to state of arousal) without exceeding threshold. It should be understood that since homogeneity criteria can be dynamically calculated based upon incoming data, that epochs which were originally rejected can become accepted, and vice-versa.

The stability of the R-AEPs is important in the estimation of threshold. As the intensity of the ramp stimulus decreases, the variance of the evoked responses will likely become larger (for both amplitude and phase), and the SNR will become worse. This variance will effect threshold estimation both when it occurs using simple SNR criteria and when the slope of the responses is used to predict threshold, for example, using regression or other means. Rather than using all the response data contained in the amplitude plots when predicting threshold, only points in the amplitude plots which exceed a certain SNR, with respect to the noise estimate, may be used in the computation of threshold. This will tend to cause the threshold estimate to be based upon the responses evoked by the higher intensity sections of the ramping stimulus.

Alternatively, two or more amplitude plots may be obtained, by organizing the sweeps in into two sub-averages (e.g., organizing odd and even sweeps into two different sub-averages), and computing the results for each sub-average. While these sub-average sweeps are combined into a single average sweep upon which the threshold estimate is determined, these sub-averaged sweeps may provide estimates of the stability of specific regions of the data. By computing the cross-correlation between, for example, 1 second of data from the amplitude plots that are computed for the two (or more) sub-averages, only the sections of the amplitude plots which have a correlation above a certain value will be used in the final averaged sweep from which the thresholds are estimated.

In an alternative embodiment the ramping test can be used as a rapid screening test. Although ramping stimuli tests may be used to rapidly provide hearing assessment for at least one stimulus at many intensities, thereby providing threshold information, this information can also be used for screening purposes, by creating a minimum intensity which defines "normal hearing" comparing the results with this to create a pass/fail result. Further, the R-AEP data can be analyzed in a time dependent fashion. For example, the R-AEPs elicited by the higher intensity R-AEP stimuli should normally become significant within, for example, 3-6 iterations of the ramping stimulus. If this does not occur, then a FAIL result can be issued, as long as the EEG-noise levels are below a specified level which can be obtained from the database, without waiting to see if the R-AEPs evoked by lower intensities of the ramping stimulus will become significant at a later point in time.

Iterative Ramping Tests

The ramping tests previously described herein, and in the prior art, evaluate the threshold at the end of a recording procedure. The testing procedure may be terminated when the SNR characteristics of the averaged waveform reach specified criteria such as the noise falling below a level specified within the normative database, or may be terminated after a certain amount of time. After the test has completed thresholds are estimated from the final data.

Figure 6:
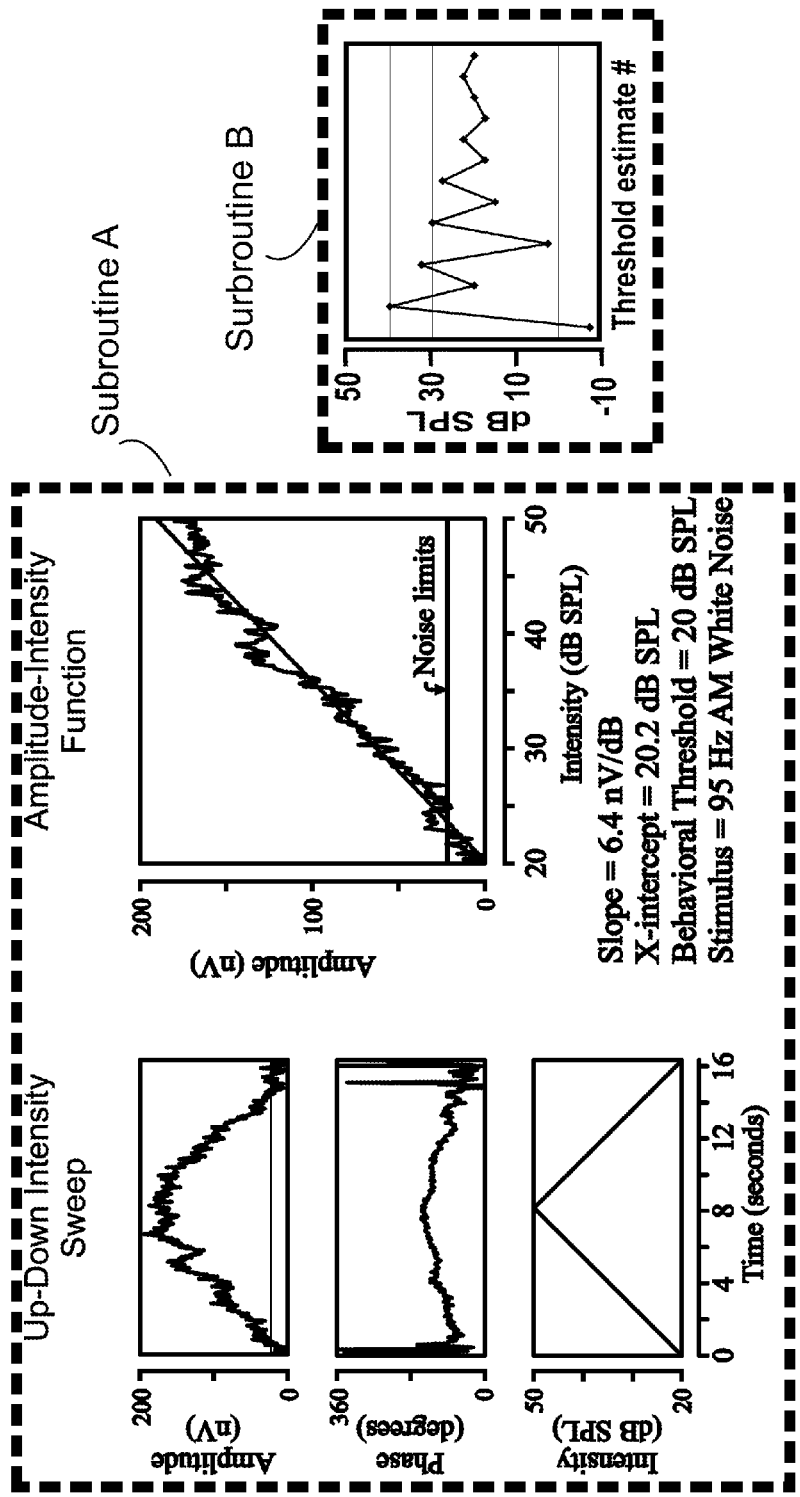
FIG. 6 shows an iterative testing procedure having subroutine A and subroutine B in which subroutine A includes performing a ramping test and estimating a hearing threshold, and subroutine B includes generating a threshold series wherein s subroutines A and B are iteratively repeated until statistical analysis performed in subroutine B indicates that the results meet a criteria and the testing of that stimulus can be stopped.
Figure 6:
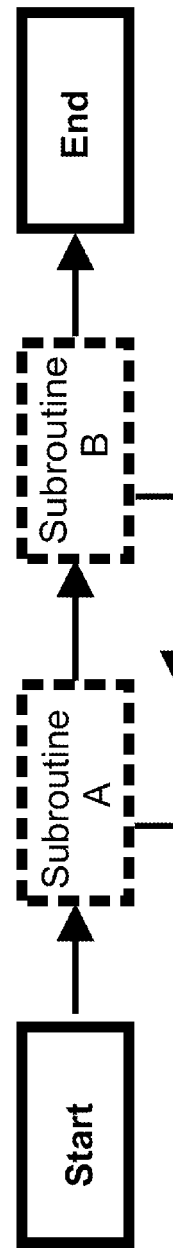

This type of procedure may not provide an indication of how stable the threshold estimate is. Further, this type of procedure may require more time than is necessary. FIG. 6 shows an example of an iterative ramping test performed by the auditory evaluation program 40 which offers advantages over this procedure. In subroutine A, a ramp stimulus is presented, the mean data are analyzed, and a threshold is computed. In subroutine B, the threshold is added to a "threshold series". These two subroutines are repeated until the threshold series, or a portion of the threshold series (e.g., the last 5 estimates) meets one or more criteria, such as being below a specified variance estimate (e.g., standard deviation, co-efficient of variation, or percentage change from last estimate). The variance estimate of the threshold series can be iteratively computed upon data such as, the cumulative averaged sweep, the individual sweeps, or a set of sub-averages of the sweeps. A variance of the threshold series, or portion of the series, may be used in the computation of the confidence limits of the estimated threshold.

Epochs can be rejected if they fail to meet homogeneity criteria, such as an inter-sweep noise criteria. As discussed previously, homogeneity criteria can be adjusted based upon the characteristics of all the epochs which have already been collected. Because the size of the signal changes as the characteristics of the ramping stimuli change, homogeneity criteria can also be created for each column of epochs in the data matrix, and can be adjusted independently for each column ("intra-column homogeneity criteria"). Intra-column homogeneity criteria are based upon SNR estimates, or the energy estimated in the signal bin (i.e., a limited amount of data, corresponding to the time of an individual epoch, from a row of the spectrogram data), while homogeneity criteria based upon background EEG-noise levels can span across columns since this measure should not change with the stimulus. Homogeneity estimates here include fft bin-noise, and SNR estimates as discussed above. Data matrix definitions include rows and columns. Weighted averaging, the zero replacement technique, swapping replacement technique, repeating replacement technique can all be relied upon in this procedure. Intra-sweep criteria may be used to reject data from an entire sweep, for example, if more than 3 epochs are replaced due to failing to meet inter-epoch criteria, and the sweep still contains a much different amount of noise than the other sweeps, it can be removed from the data. If a sweep is removed from the data then any threshold estimate that was based upon the sweep can be retro-actively removed from or modified in the threshold series.

Dynamic Iterative R-AEP Tests

Figure 7:
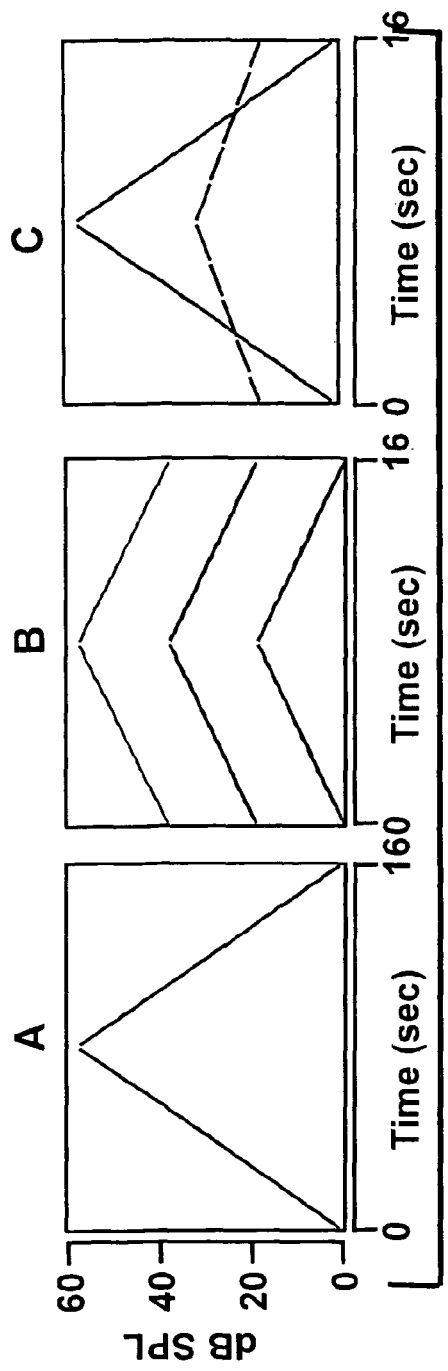
FIG. 7 shows the instantaneous intensities of ramp stimuli that are used for an embodiment of a method for iterative testing and an embodiment of a method for accomplishing a Dynamic Iterative Ramp Test.

In addition to performing the R-AEP tests in an iterative manner, the actual stimuli can be changed dynamically within a testing procedure. FIG. 7 shows examples of three methods of performing a ramping test. In column A of the figure, the standard ramping stimulus is used in an iterative manner as described above. In column B, the stimuli for a Fractionated Ramp Test are shown where the full range of the stimulus has been divided into 3 smaller ranges of intensity. The first stimulus ramps between about 40 and about 60 dB SPL, with the second and third ramping stimuli being decremented in 20 dB steps. For each ramping stimulus, threshold can be estimated, and these results can be combined and analyzed as a single threshold series or can be analyzed as several independent threshold series. In column C, an Adaptive Fractionated Ramp Test is shown, wherein a ramp stimulus with a large range is first used to obtain an estimate of threshold, and then a second ramp stimulus is used where the ramp ranges above and below this estimated threshold by, for example, +10 dB and −5 dB respectively, and the slope of the ramp has been decreased. The base signal is the same for the two ranges of intensity ramps.

The fractionated intensity ramp technique and the adaptive fractioned intensity ramp technique are useful because they allow more data to be collected in an intensity range of interest, which can allow for a more accurate estimate of threshold. When the intensity of the stimulus is very far above threshold, a stable estimate of response amplitude can be obtained quickly, and so not much data may be needed at that range to provide an initial rough estimate of threshold which can be explored using ramping intensity ranges that are appropriate for that subject. Using a dynamic or adaptive technique is advantageous because the responses to intensities that are very far above threshold, may be less accurate in determining threshold, than the medium intensity levels closer to actual threshold. Further, responses obtained in response to lower intensity stimuli may not be above the noise floor and may be below the subject's threshold. Accordingly, by causing the intensity ramp to straddle the area of estimated threshold the data that is recorded can be more relevant and can offer a more reliable estimate of threshold.

Figure 8:
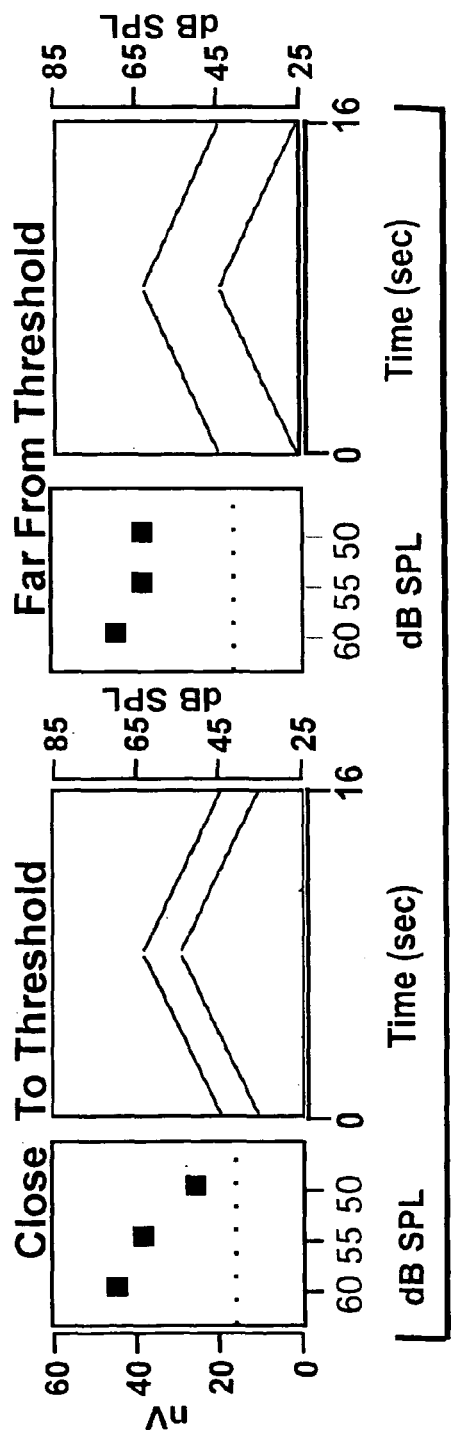
FIG. 8 shows an example of evoked response data, noise estimates, and the range of instantaneous intensity of stimuli used in an embodiment of the Dynamic Iterative Ramp Test, which is based upon response data.

In FIG. 8 an Adaptive Fractionated Ramp Test is used wherein the lower intensity ramping stimulus is adjusted based upon the signal and noise characteristics of the first test. In the example shown on the left, the averaged sweep collected in response to the first intensity ramp produces some evoked responses that are "close to the threshold" of the subject, e.g. within approximately 110-250%. In addition to a threshold series, estimates of the amplitude of the response at 60, 55 and 50 dB SPL are obtained by windowing the averaged sweep appropriately. The decrease in response amplitude from 60 to 55 dB SPL is not much, but the decrease from 55 to 50 brings the amplitude of the response close to the noise floor. This suggests that the lower intensity ramp stimuli are approaching threshold. Accordingly, the range of the subsequent ramp stimulus is decremented only slightly, e.g., by about 5 dB, or not at all.

In the second example, on the right of FIG. 8, the first intensity ramp produces responses that are "far from threshold", e.g. within approximately 210-250%. The responses to the lower intensities of the stimulus are considerably above the noise floor. Accordingly, the range of the subsequent ramp stimulus is decremented by about 10 dB. While the examples show only two repetitions of the adaptive fractionated ramp procedure, more repetitions are possible.

In order to reach significance using an F-ratio (df 2,240), the amplitudes of the evoked responses must be a certain amount, e.g., about 170%, of the size of the background EEG noise level estimate. Depending upon the type of stimulus used, a change in intensity can produce a certain decrease in the amplitude of the responses e.g., decrease of about 20% for every 10 dB decrease in intensity. The reduction in intensity can be based upon an expected decrease in the amplitude of the evoked response which would occur with a given change in intensity. For example, below 70 dB SPL, the decrease in amplitude which occurs with intensity is about 2 nV/dB, while for noise the reduction is likely 2-4 times this. Normative values for the average decrease in amplitude which is associated with a specified decrease of intensity, based upon the parameters of the ramping stimulus, can be stored in the database. In one embodiment, the mean amplitude, of the R-AEPS evoked by the highest ⅓ of intensity range of the ramping stimulus, is used to adjust the maximum intensity of the subsequent ramping stimulus, so that the R-AEPS evoked by this intensity region are, for example, 250% above the noise floor.

Accordingly, in one embodiment of the invention, a method of testing auditory function according to the dynamic iterative ramp test procedure comprises:

a. acoustically presenting at least one ramp stimulus having an intensity range to at least one ear of a subject;
    b. recording response data epochs of ramping evoked potential response data;
    c. classifying the response data epochs into accepted epochs and rejected epochs where the response data epochs are classified as rejected if the epoch fails to meet a homogeneity criteria;
    d. performing time-frequency signal analysis on the acceptable response data epochs to generate result data;
    e. performing steps "a-d" iteratively until criteria such as a noise level criteria or a time criteria has been met.
    f. using the result data to determine a preliminary audiometric threshold estimate and using this estimate to determine a useful intensity range for a second ramp stimulus or using the signal to noise levels of the result data to determine a useful intensity range for a second ramp stimulus;
    g. performing steps a-d iteratively, and on each iteration, the estimate of the subject's threshold is included in a threshold series for the intensity range, with the iterations being completed when the threshold series meets specified threshold criteria.

In step f, using the result data to determine a preliminary audiometric threshold estimate can utilize the threshold estimated from a threshold series.

As has been described previously, in all of the ramping stimulus methods described, the R-AEP data for each of the different ramp stimuli are organized, stored, and analyzed in separate data matrices, although the information from each of these data matrices can be combined and analyzed as a whole in order for the software to provide the final results of the testing procedure. Further, it should be understood that the epochs or sweeps may be identified for noise reduction according to one of the homogeneity criteria described here, such as the inter-epoch noise criteria within or across sweeps, etc. The identified epochs can then be processed according to one of the noise reduction schemes described here such as the zero replacement technique, the swapping replacement technique, etc.

Figure 9:
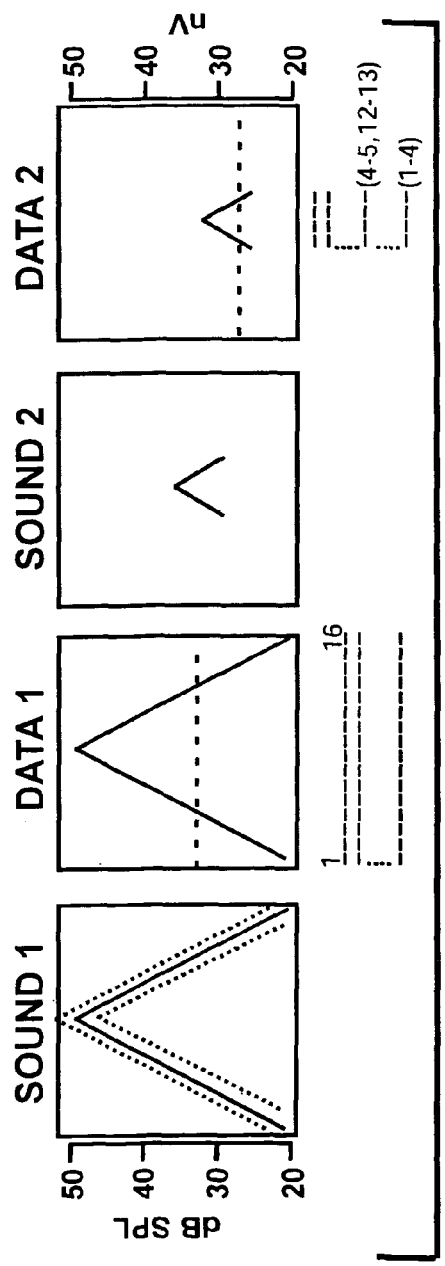
FIG. 9 shows an example of how stimuli may be selected in a Dynamic Iterative Ramping Test, based upon response data, and shows an example of the Dynamic Linked Ramping Test technique.

In the dynamic iterative ramp tests that have been described, the data collected to the different ramp stimuli are stored and analyzed in different data sets. Accordingly, when analyzing the data evoked in response to the second stimulus, the raw data recorded from the first ramp stimulus is usually ignored. This can be less efficient than desired and can be countered in the following variation to the Dynamic Iterative Ramp Test procedure. FIG. 9 shows an example of the Dynamic Iterative Linked Ramp Test technique. The left two graphs of FIG. 9, show the instantaneous intensity of the ramp stimulus and hypothetical amplitude of the evoked response data, both as a function of time, for an iterative ramping test with a single ramping stimulus. Additionally, the dotted lines on the intensity ramp of the stimulus (labeled "sound 1") show the range of the stimulus that evoked responses at that same point in time for the average sweep data. When using a signal processing technique to convert the time series data (the averaged sweep) into a spectrogram, such as short time frequency analysis which works by iteratively moving a window through the time series data, the length of the window determines the characteristics of the resulting spectrogram. As the data window used to make the spectrogram increases, the range of the sound which evoked the response amplitudes that are plotted for a corresponding moment in time on the data graph increases. In the graph of the response data (Data 1), the noise estimate has also been plotted. The amplitudes in epochs 4 and 5 produce responses that are below and above the noise floor, respectively. On the downward ramp the signal falls below the noise floor between epochs 12 and 13. Epochs 4 and 5 can be referred to as a first threshold straddle epoch pair and epochs 12 and 13 can be referred to as a second threshold straddle epoch pair. The range of the intensity ramp for the stimulus for the first and second threshold straddle epoch pairs is used to make a symmetrical ramp stimulus shown in the graph labeled Sound 2. The epochs from columns 4, 5, 12 and 13 are extracted from the data set obtained using sound I (i.e., the Data1 set) and are used to create sweeps of 4 rather than 16 epochs. The new data evoked by the ramp stimulus of Sound 2 is then stored in sweeps of 4 epochs that correspond the same intensity range of Sound 1. Accordingly, using this technique the data evoked by the first stimulus can be used during the entire testing procedure.

In one embodiment, the method of testing auditory function using a Dynamic Iterative Linked Ramp Test procedure comprises:
a. acoustically presenting at least one ramp stimulus having an intensity range to at least one ear of a subject;
b. recording evoked response data organized into epochs;
c. classifying the epochs into accepted epochs and rejected epochs where said an epoch is classified as rejected if the epoch fails in meeting a homogeneity criteria;
d. performing time-frequency signal analysis on the accepted epochs in order to generate result data,
e. performing steps "a-d" a specified number of times
f. using the signal to noise levels of the result data to find the first and second threshold straddle epoch pairs and determine the corresponding intensity range for use in a second ramp stimulus;
g. rejecting all data epochs that were just recorded which do not correspond to the intensity range of the second ramp stimulus, and reorganizing all remaining data epochs so that they correspond with the data that will be collected with the second ramp stimulus;
h. performing steps "a-d" iteratively using a second ramp stimulus, and on each iteration, the subject's estimated threshold is included in the threshold series for the intensity range; the iterations being completed when the threshold series meets specified threshold criteria.

The examples used thus far for ramping intensity tests have been illustrated using a single ramping stimulus, for at least one ear. As in the case of the MASTER technique, it is possible to test several ramping stimuli at once and simultaneously obtain frequency specific data for multiple frequencies. For example, four amplitude modulated carrier frequencies can be created and then turned into intensity ramping stimuli by multiplying each of these modulated stimuli by a ramping function. After the ramping stimuli have been created they can be added together, for example, digitally or acoustically, and then presented to an ear of the subject.

It is also known that different carrier frequencies evoke SS-AEPs of different sizes. For example, at a stimulus modulation rate of 80 Hz, the responses to amplitude modulated carrier frequencies of 500 Hz are smaller than the responses obtained to amplitude modulated carrier frequencies of 1000 Hz. Accordingly, the ranges and ramping functions (e.g., slopes) may be different according to the carrier frequency of each ramping stimulus that is combined into a multiple ramping stimulus that is presented to an ear of a subject. Pilot data, using the MASTER technique, has shown that SS-AEPs can be successfully obtained to multiple stimuli presented simultaneously, when each carrier presented at a different intensity, as long as the different intensities did not differ by more than 20 dB. Accordingly, in one embodiment, the range of the intensity ramps for the different ramping stimuli should not differ by more than 20 dB.

Figure 10:
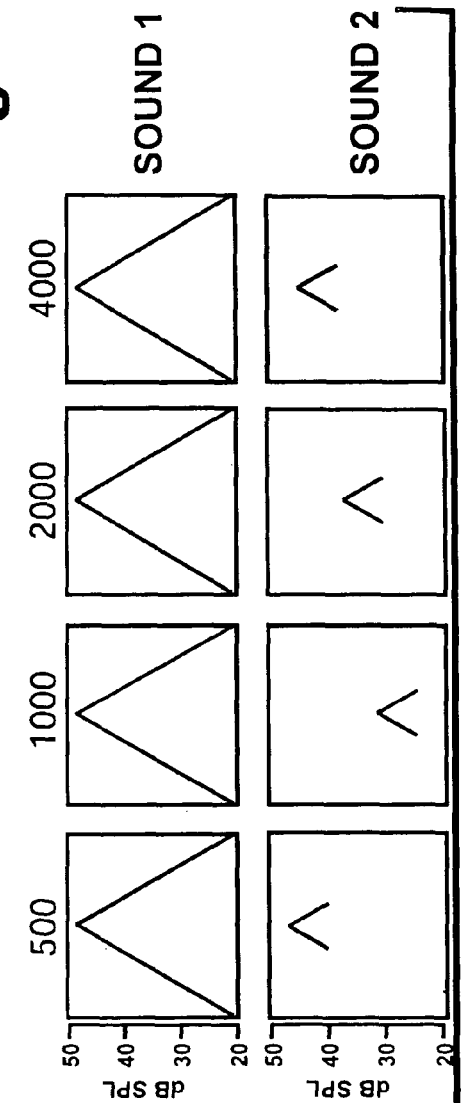
FIG. 10 shows an example of how stimuli may be selected in a Dynamic Iterative Ramping Test, based upon response data, when multiple frequency specific stimuli are tested at the same time.

FIG. 10 shows the same procedure that was demonstrated in FIG. 9, but now applied to the case where multiple stimuli are presented, simultaneously, to an ear. This technique can also be applied to binaural testing, but is simplified for this example. In FIG. 10, the Iterative Dynamic Linked Ramping Test first uses ramping stimuli which each have the same intensity range for the 4 carrier frequencies being tested. Based upon the analysis of the averaged response data obtained from these ramped stimuli, a second set of ramped stimuli is created. For example, the 500 Hz evoked response data suggested that a threshold existed near 42 dB SPL. The epochs from columns 6, 7, 14 and 15, in the response data was combined into sweeps of 4 epochs and the responses to the second ramping stimulus were averaged with this data. For the 1000 Hz evoked responses, epochs from columns 2, 3, 10, and 11 were concatenated into the sweeps of the data set used to evaluate the responses to the subsequent ramp stimulus. This is performed in a likewise fashion for the ramping stimuli with carrier frequencies at 2000 and 4000 Hz.

Similar to an embodiment of the MASTER technique where the intensities of the multiple stimuli are dynamically changed as the associated SS-AEPs reach significance, the audiology test program 40 organizes the data matrix so that epoch recorded to different stimuli and/or different intensities of the stimuli can be analyzed independently.

Modulation Optimization Test (MOT)

In order to perform an SS-AEP threshold or screening test, or a RAMPER test more efficiently it can be beneficial to utilize modulation frequencies which produce the largest signal to noise level for a given subject. For example, Sturzebecher et al, (2003) has recently shown that, at least for click stimuli, the 140 Hz range, rather than the 80-100 Hz range, provided the most robust responses in a group of infants. These types of "peaks and valleys" in the size of the responses over a range of modulation rates have been noted by others. Using a "good" modulation rate will result in response that has much better SNR as a "poor" modulation rate. Accordingly, in order to perform an SS-AEP or RAMPER test, it may first be beneficial to generate a modulation transfer functions using tonal, noise or click stimuli and then use optimum modulation frequencies when performing the actual test.

Further, the optimum modulation frequencies for specific carrier frequencies cab be computed (i.e. predicted) based upon the optimum modulation frequencies obtained to click stimuli. For example, if the optimum modulation frequency is 110 Hz using click or noise stimuli, then the lower carrier frequencies of the test stimulus, e.g., 500 Hz and 1000 Hz should be modulated at 100 and 105 Hz, while the higher frequencies, e.g., 2000 and 4000 Hz stimuli should be modulated at 120 and 125 Hz. The results of the MOT test can be interpreted utilizing age-appropriate population norms. For example, the prediction of the optimum modulation rates for certain modulated carriers, which is made using the optimum modulation frequencies obtained using click stimuli, can be predicted as a function of age.

The MOT procedure can be used to optimize the subsequent ASSR, MASTER, or RAMPER testing protocol by using modulation rates that produce good SNRs. Additionally, these testing protocols become more sensitive because they avoid the low SNR frequency ranges, or the "null sections", of an individual, which can cause incorrect identification of hearing impairment, when these tests are performed without an MOT test. The MOT test can be performed in a rapid manner by using a greater stimulus intensity than would be used during the subsequent ASSR, MASTER or RAMPER tests. For instance, a MOT test can be completed in approximately 3-5 minutes.

To facilitate the MOT test, the ramping methodology described here is applied to the modulation frequency. The MOT procedure can be done binaurally, in which the stimuli to the left and right ears may be the same, or the ramping functions for the stimuli presented to the two ears may be different. For example, the modulation frequencies for the left ear may ramp from 20 to 100 Hz while the modulation frequencies for the right ear may ramp from 100 to 200 Hz. In this manner, a greater range of modulation frequencies may be tested. Alternatively, if the RAMP is the same for both ears, e.g. 20 to 100 Hz, the size of the evoked response data for the binaural stimulus is larger. Alternatively, the ramp may be limited to a small range of modulation rates, such as 75 to 100 Hz. In the case where the modulation frequency is ramped from 20 to 100 Hz, if the sweep lasts 8.192 seconds then the modulation rate may change by 10 dB per epoch, whereas if the sweep lasts 16.384 seconds, then the modulation rate will change by 4 dB per epoch. As with any characteristic of a ramping stimulus, the rate of the stimulus parameter which is being ramped will depend upon the shape of a ramping function range of the parameter which is being modified and the sweep length. (e.g., the range of the modulation frequencies to be tested, and the duration of the sweep to be analyzed, will determine the rate of the change of modulation within the ramping stimulus.) The Data Quality Control Techniques which were described for the intensity ramping tests can be applied to the MOT test as well.

In one embodiment, a method of utilizing a modulation optimization test in order to increase the efficiency, specificity, and sensitivity of an ASSR, MASTER, or RAMPER test comprises:
  a. performing a modulation optimization test to produce result data in which the instantaneous modulation frequency of the stimuli are ramped according to a ramping function.
  b. analyzing the result data to derive at least one modulation rate with good SNR characteristics: and;
  c. using the at least one modulation rate with good SNR characteristics from step b in an auditory-test such as an ASSR, MASTER, or RAMPER test.

In alternative embodiment of the MOT test, rather than using a ramping stimulus with a continuous ramp, the ramping function is created as a staircase where a different modulation frequency is tested during each epoch. Alternatively, and SS-AEP test is done where the modulation rate is sequentially changed several times during a test. In these alternative embodiments, the steps can be summarized as
  a. obtain amplitude or SNR estimates for several modulation frequencies using stimuli which will create large responses and/or which are presented at loud intensity levels.
  b. choose at least one modulation frequency from the modulation rates showing the larger amplitudes or SNRs in a subsequent audiometric test which utilizes SS-AEP or R-AEP stimuli.

R-AEP Fine-Structure Test and RAMPER Masking Test

Instead of ramping stimulus intensity over time to determine the hearing thresholds of a subject in order to generate an audiogram, other capacities of the subject to detect other characteristics of the stimulus can be tested using the testing methods already described, which use time-frequency analysis techniques and ramping stimuli. For example, the fine structure of the audiogram may be evaluated using a R-AEP Fine-Structure Test. In the Fine-Structure Test, a single modulation rate is used while the frequency of the carrier signal is ramped, for example, increasing the carrier frequency over time, from a low frequency (e.g. 200 Hz) to a high frequency (e.g. 4000 Hz). The carrier's instantaneous frequency can be ramped in a linear, logarithmic, chirp or other function, or may consist of more than one function. The carrier can be signals other than tones, such as band-limited noise whose center frequency is ramped over time. Since the modulation rate remains fixed, only the change in carrier frequency over time should affect the relative amplitudes of the evoked responses at different moments in time. In an alternative embodiment as the ramping stimulus changes frequency it simultaneously follows an intensity ramp so that the intensity of the stimuli remain constant with respect to a specified intensity type (SPL, nHL, HL). In an alternative embodiment for different signals, each modulated at a different rate, are ramped simultaneously. For example, stimuli 1-4 can simultaneously ramp from 250-750, 750-1500, 1500-3000, and 3000-6000 Hz, respectively. While the relative R-AEPS to the four ramping stimuli should not be compared, since R-AEP size is a function of modulation rate, the R-AEP results for each frequency can provide an estimate of the fine structure of the audiogram. The Fine-Structure Test can be done at several times at one or more intensity ranges. The results of the Fine-Structure Test, such as the time-frequency results, the amplitude and phase plots, and the summary results can be compared to normative values for measures such as the average slope of the R-AEP amplitude between the 1000 and 2000 Hz. Homogeneity criteria related to the background EEG-noise levels can be used to increase the fidelity of the test.

In a variant of this test, termed the RAMPER Masking Test, two types of stimuli are presented to an ear. The first stimulus is termed the "test" stimulus and is a steady-state stimulus, for example a 1000 Hz tone modulated at 80 Hz, the second stimulus is a ramping stimulus, whose carrier frequency changes over time between two frequencies, for example, from 500 Hz to 2000 Hz with an instantaneous frequency that follows a ramping function. The ramping stimulus may be modulated or un-modulated and may be at the same intensity as the steady-state stimulus, or may be slightly higher or lower in intensity. In this test, the ramping stimulus serves as a masker for the steady-state stimulus, and based upon the changes in amplitude that occur over time in the spectrogram-based analysis, a function can be generated which should approximate the functional (i.e. physiological) tuning curve for the frequency region of the test stimulus.

A basis of this technique was reported by the Inventor in John et al (1998), where interactions between stimuli were investigated by measuring the amplitude of a steady-state response which was attenuated or amplified by the presence of another steady-state stimulus. Utilizing the physiological measurement of the interactions which occur between stimuli, as a diagnostic test has not been suggested, and is novel. Further, in one embodiment segments of the physiological tuning curve generated from this test can be analyzed in several ways, for example, the slope of certain segments of the curve can be measured and compared to appropriate population normative data. This comparison can lead to a normal/abnormal result. The use of a RAMPER technique and associated time-frequency spectrogram-based analysis, used with homogeneity criteria and EEG-noise level criteria, should reduce the time needed for this type of test and provide for a more reliable audiometric assessment.

Additionally, in an embodiment of the technique, rather than presenting the ramping masker stimulus in conjunction with a single probe stimulus, multiple probe stimuli can be presented as occurs in the MASTER technique. Accordingly, while the masker stimulus moves away from the critical band of a probe stimulus at 500 Hz it will simultaneously be moving towards the critical band of a probe stimulus at 1000 Hz. The data quality control techniques which were described for the intensity ramping tests can be applied to these tests as well.

Multiple Intensity Test for Estimating Threshold

A method is used to achieve a rapid estimate of a patient's hearing threshold by evaluating hearing at several intensities simultaneously. In an embodiment of this test, a stimulus is created from several individual stimuli each of which is characterized by a different intensity and modulation rate, and which are combined and simultaneously presented to the patient's. This type of stimulus is referred to as a Multiple Intensity Stimulus. For example, in the case of amplitude modulated stimuli, several modulation functions are used each having their own intensity envelopes and modulation frequencies. These can be each be applied to a noise carrier (e.g., BBN, HPN, etc.) to produce an amplitude modulated noise stimulus.

An example of how to make a multiple intensity stimulus is as follows: 2 or more modulation envelopes of different amplitudes (i.e., intensities) are combined and multiplied with a noise carrier signal to produce a stimulus that is modulated at two different rates, each rate having a unique intensity. The modulation depth can be 100%. The response data evoked by this stimulus will contain responses evoked by stimuli at the different intensities. One difficulty with this technique is that the 2 or more modulation envelopes may serve to activate the cochlea at the same time and thereby reduce the response to each of the envelope components. This can be seen in the top panel of FIG. 11, which shows a multiple intensity stimulus which was created using three sinusoidal AM envelopes and a noise carrier. The modulation rates for the three different intensities tested were separated by about 5-6 Hz. As indicated in FIG. 1, the modulation rates were 80.08, 84.96, and 91.8.

In an alternative embodiment of the Multiple Intensity technique, the simultaneous activation of the cochlea is diminished by using exponential envelopes with closely spaced modulation frequencies. The choice of phase values, for the modulation functions, can also be important and correctly chosen phase values. An example of stimuli produced with these characteristics are shown in the second panel of FIG. 11. Unlike the stimulus in panel 1, in this example, where 3 envelope functions were generated by exponential envelopes with the exponential set at 10, produces less overlap: the three modulation envelopes, each with its own amplitude (intensity) can be visually detected. Alternatively, using 2 envelope functions which are 180 degrees out of phase, and which have closely spaced modulation frequencies produces a multiple intensity envelope with better characteristics (stimuli not shown), because the different intensities stimulate the cochlea at different times for a greater portion of the stimulus.

Figure 11:
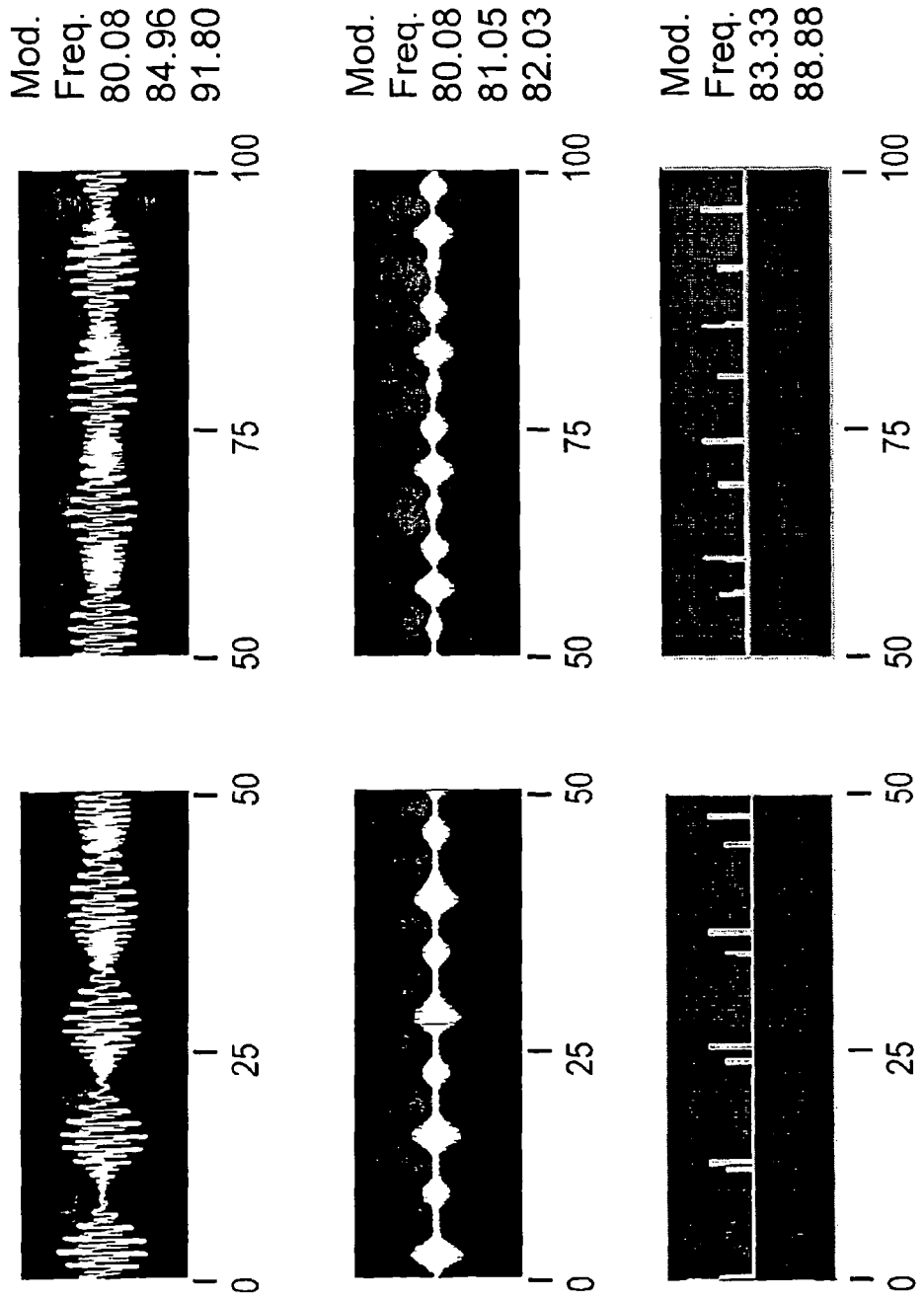
FIG. 11 shows examples of multiple intensity amplitude modulated noise stimuli that were created using sinusoidal or exponential envelopes (and well chosen stimulus parameters), or which were created using clicks.

In another embodiment, the testing method addresses the issue of simultaneous activation of the cochlea, by using rapid transient stimuli rather than steady-state stimuli. Multiple transient stimuli can be simultaneously presented at different repetition rates, where each rate has a different intensity. Each of the repetition rates should have inter-stimulus intervals (i.e., the time between the start of sequential stimuli) that are integer sub-multiples of the epoch length as was described previously in this material. The $3^{rd}$ panel of FIG. 11, shows a multiple intensity stimulus using clicks at 2 intensities.

Each column in the figure shows the stimulus over a 50 msec period, with left spanning 0 to 50 msec and the right spanning 50 to 100 msec. In the upper panel of FIG. 11, the 3 stimuli show considerable overlap, while in the middle panel the individual 3 envelope functions of different intensity are more discrete. The bottom panel shows the least amount of overlap due to the rapid presentation time of the stimuli.

The responses to a multiple intensity stimulus can be used as a screening test, by examining whether the response to a stimulus at a particular intensity is significant. For example, a screening test can consist of 3 intensities being tested at once, where the middle intensity or lowest intensity is defined as the "screening" intensity If the subject does not show a response to the screening intensity, but does show a response to a higher intensity stimulus, which, for example, may be 7 dB above the middle intensity stimulus, then this may indicate that while the subject failed the screening test, hearing is almost normal. This may avoid the necessity of a subsequent test being necessary. This advantage of this test is similar to that which is obtained for a ramping stimulus technique, in that it may act as a compromise between a screening and threshold test, whereby if the subject doesn't show evoked responses to an intensity level that is defined as normal for screening, information regarding the subject's threshold is available to inform the medical personnel about how bad the hearing loss may be. Unlike the use of a ramping stimulus, the multiple intensity stimulus is presented simultaneously and at a limited number of intensities. The separation between the lower to middle intensity and middle to high intensity can be identical, or can be different.

The Multiple Intensity Stimulus Test can also be used to estimate threshold either by considering the significance of the evoked responses directly or by fitting the response data with appropriate regression equations. Because some masking of the simultaneously presented stimuli may occur due to the temporal overlap and temporal proximity of the stimuli, a weighting factor, or set of weighting factors for each intensity can be multiplied with each of the evoked responses from this test prior to their evaluation by means of, for example, regression. For example, the amplitude of the responses can be multiplied by a weighting factor, which can be based upon normative data, for example, 110%, in order to compensate for decreases in amplitude due to masking. The issue of masking can also be addressed by presenting the multiple intensity stimuli at higher intensity ranges than are normally used in screening tests, if it can be shown that the information obtained at these higher intensities is relevant to an estimation of actual behavioral thresholds.

The system and methods described here can be used to provide a rapid, reliable, and automatic tests of hearing. These tests include initial screening evaluations and threshold testing which can be based upon either frequency-specific or non-frequency-specific criteria. These tests include assessing many capacities of an individual's auditory system.

Novel types of SS-AEP tests and R-AEP tests utilize stimuli such as modulated noise and transient stimuli, such as clicks that are presented at carefully selected repetition rates. The stimuli described evoke large steady-state responses and thereby increase the speed of the automatic testing procedure. Methods are described wherein the characteristics of the test stimuli can be changed, during a test, for example, based upon data collected in an early part of the test.

Novel types of methods for processing, accepting, and rejecting the evoked response data are described. Data Quality Control Techniques increase the reliability and stability for the estimates both of the evoked responses and of the background EEG-noise levels. Homogeneity criteria are described.

Novel statistical methods are described which increase the accuracy of the tests. Some tests utilize significance series in order to decrease the occurrence of false positives and false negatives. Some tests utilize a threshold series in order to asses the stability of each threshold estimate and to determine how long a test must continue.

Additionally, the use of ramping tests which rely on rapidly presented ramping stimuli to evoke ramping auditory evoked potentials is also described. Ramping tests can provide a rapid and objective estimate of threshold for either frequency specific or-non-frequency specific stimuli. By performing homogeneity testing on the data, rather than simple artifact rejection criteria, the phase and amplitude plots, which provide a measure of the signal at different moments in time, can be used to obtain a better estimate of threshold. Additionally, a novel equation is used to make the phase data of the spectrogram useful in the detection of the response.

Further, multiple intensity tests are described which can be used to obtain a quick screening test, as well as providing some information about a subject's threshold. The tests described often are performed with multiple stimuli and can be used to test both ears simultaneously.

Rather than utilizing the R-AEP tests and methods described here, which use a continuously changing acoustic stimulus and time-frequency analysis, the R-AEP tests can be approximated or "mimicked" by obtaining a series of sequential recordings each of which use discrete stimuli and analyzes result data using only frequency analysis. This less desirable method, may, in some cases approximate the information that can be obtained using the ramping stimuli, signal processing analysis techniques, and time-frequency analysis of the R-AEP tests, but will require more time, be less accurate. However, the Data Quality Control Techniques described herein, can be applied both within and across this series of sequential tests to improve the data quality, and therefore improve Test Results.

The presently described embodiments of the hearing evaluation systems and methods offer advantages over prior art. Although modifications and changes may be suggested by those skilled in the art, it is the intention of the inventor to embody within the patent warranted herein all changes and modifications as reasonably and properly come within the scope of their contribution to the art. The titles, headings, and subheadings provided in this specification are provided for organizational purposes only and are not meant to restrict the invention in any way, nor to limit material described in one section from applying to another section as would be apparent to those skilled in the art.

Several of references have been described in this patent specification. A full citation is presented below and the contents of the cited references are hereby incorporated by reference herein.

REFERENCES

Patent Application:
PCT/CA 01/00715 John and Picton, System and Methods For Objective Evaluation Of Hearing Using Auditory Steady-State Responses.
Published Abstracts:
John, M S., Brown, D., P. Muir, P., & Picton, T. W., Use of Modulated Noise in Newborn Hearing Screening. International Evoked Response Auditory Study Group (IERASG), 2003b.
Perez-Abalo, M. C., Savio, G., Gonzlez, m, Hernndez, O., Ponce de Leon, M., and Eimil, E., Hearing Screening with Multiple Frequency Steady-State Responses: A Pilot Study. International Evoked Response Auditory Study Group (IERASG), 2001.
Scientific Publications:
John M. S, Dimitrijevic, A., and Picton, T. W. Efficient Stimuli for Evoking Auditory Steady-State Responses, Ear and Hearing, 24(5):406-23, 2003a. John M. S., Dimitrijevic, A., and Picton, T. W. Weighted averaging of steady-state responses. *Clinical Neurophysiology,* 112:555-562, 2001.
John, M. S., and Picton, T. W. MASTER: A Windows program for recording multiple auditory steady-state responses. *Computer Methods and Programs in Biomedicine,* 61, 125-150, 2000.
John, M. S., Lins, O. G., Boucher, B. L., and Picton, T. W. Multiple auditory steady state responses (MASTER): Stimulus and recording parameters. *Audiology,* 37:59-82, 1998.
Linden R D, Campbell K B, Hamel G, Picton T W. Human auditory steady state evoked potentials during sleep. Ear Hear. 1985 May-June;6(3):167-74.
Norcia A M, Tyler C W. Spatial frequency sweep VEP: visual acuity during the first year of life. Vision Res. 1985;25(10): 1399-408.

REFERENCES

Scientific Publications (Continued):
Picton T W, Dimitrijevic A, John M S, Van Roon P. The use of phase in the detection of auditory steady-state responses. Clin Neurophysiol. 2001 September;112(9):1698-711.

Rees A, Green G G, Kay R H. Steady-state evoked responses to sinusoidally amplitude-modulated sounds recorded in man. Hear Res. 1986;23(2):123-33.

Stapells D R, Oates P. Estimation of the pure-tone audiogram by the auditory brainstem response: a review. Audiol Neurootol. 1997 September-October;2(5):257-80. Review.

Books:

Zar J H. Biostatistical Analysis. Fourth edition. Upper Saddle River: prentice Hall, 1999.

I claim:

1. A method of performing an auditory screening test on a patient by operating a system for performing objective audiometry, the method comprising:
   a. operating a processor of the system to acoustically present at least one modulated noise stimulus at a screening intensity to at least one ear of the patient;
   b. operating the processor to provide recording of response data related to the patient's response to the at least one stimulus;
   c. operating the processor of the system to perform signal analysis on said response data to generate result data;
   d. operating the processor of the system to evaluate the result data using at least one statistical test to determine the presence of at least one auditory steady-state response; and,
   e. operating the processor of the system to provide a pass/fail test result which indicates whether said patient has passed or failed said screening test, whereby the patient is assessed with normal hearing for a pass result.

2. The method of claim 1, wherein the at least one modulated noise stimulus includes at least one of: amplitude modulated broadband noise (BBN), amplitude modulated bandpass noise, amplitude modulated high-pass noise (HPN), and enhanced high-pass noise (EHPN).

3. The method of claim 1, wherein for step (d) the statistical technique includes generating a significance series by sequentially analyzing portions of the response data to generate a significance series of probability values for the at least one auditory steady-state response, and subjecting the significance series to a statistical conditional criterion to determine the presence of the response.

4. The method of claim 3, wherein said subjecting significance series to a statistical conditional criteria includes using at least one of: a consecutive count, a relative count and an adjusted critical value.

5. The method of claim 3, wherein said subjecting to a statistical conditional criterion includes using at an absolute count.

6. The method of claim 3, wherein the statistical conditional criterion is a significance value that is adjusted in relation to the number of comparisons being made.

7. The method of claim 3 wherein the statistical conditional criteria is at least one of a consecutive count and a relative count.

8. The method of claim 1 in which step (c) includes:
   (i) forming a plurality of epochs if response data using said response data;
   (ii) forming a plurality of sweeps of the response data by concatenating the plurality of epochs of response data;
   (iii) classifying each epoch of response data selected from the plurality of epochs of data as a rejected epoch if the epoch of data fails to meet one or more of the following criteria: having an SNR level above a specified value for at least one specified frequency bin of an amplitude spectrum of the epoch of data; and having an inadequate value for passing a homogeneity criteria;
   (iv) forming a plurality of accepted sweeps of the response data by concatenating the plurality of non-rejected epochs of data; and
   (v) converting the accepted sweeps into the frequency domain to generate said result data.

9. The method of claim 8, wherein the homogeneity criteria include at least one of the following: intra-sweep homogeneity criteria which are adjusted based upon statistical evaluation of at least one characteristic that is measured for each epoch of data within each sweep, and intra-sweep homogeneity criteria which are adjusted based upon at least one characteristic that is measured for each epoch of data within two or more sweeps.

10. The method of claim 9, wherein the at least one characteristic that is measured for each epoch of data is at least one of the following: an estimate for EEG-noise energy, an estimate of signal energy, and an SNR estimate.

11. The method of claim 1, wherein in the case of a fail result a hearing threshold of the patient is subsequently obtained for at least one stimulus by iteratively performing steps a-d a number of times using different stimulus intensities, and during each iteration generating a significance series wherein for each different stimulus intensity, said auditory steady-state response is determined to be statistically present when selected statistical conditional criteria are met, and the lowest intensity for which a steady-state response is determined to be statistically present is used to estimate the hearing threshold for said patient.

12. A method of performing a rapid hearing screening test on a patient by operating a system for performing objective audiometry, the method comprising:
   a. operating a processor of the system to acoustically present at least one transient stimulus at a rapid periodic rate to at least one ear of the patient;
   b. operating the processor to provide recording of response data related to the patient's response to the at least one transient stimulus, wherein several epochs of response data are recorded and the at least one transient stimulus is presented at a periodic rate that provides an inter-stimulus interval that is a sub-multiple of an epoch length;
   c. operating the processor of the system to perform signal analysis on said response data to generate result data;
   d. operating the processor of the system to detect evoked responses in the result data using at least one statistical technique, said statistical technique comprising use of a significance series and a statistical conditional criterion; and
   e. operating the processor of the system to provide a pass/fail test result which indicates whether said patient has passed or failed a screening hearing test.

13. A method of testing auditory function of a patient, by operating a system for performing objective audiometry, the method comprising:
   a. operating a processor of the system to acoustically present at least one ramp stimulus to at least one ear of the patient;
   b. operating the processor to provide recording of response data epochs of ramping evoked response data related to the patient's response to said at least one ramp stimulus;
   c. operating the processor of the system to classify said response data epochs into accepted response data epochs and rejected response data epochs, said response data epoch being classified as rejected response data epochs if said response data epoch fails in meeting a homogeneity criteria;

d. operating the processor of the system to perform signal analysis and time-frequency analysis on said accepted response data to generate result data; and, e. operating the processor of the system to calculate upon the result data to estimate the subject's threshold for said at least one ramp stimulus.

14. The method of claim 13, further comprising substituting said rejected response data epochs with new epochs using at least one of: a zero replacement technique, and a swapping replacement technique, wherein said new epochs are classified as accepted response data epochs.

15. The method of claim 14, wherein the zero replacement technique comprises substituting values of rejected epoch with zeros, and also comprises reducing the total number of counted sweeps by one when computing an average.

16. The method of claim 14, wherein the swapping replacement technique comprises replacing epochs of data epochs from a different sweep which is synchronized in a similar fashion to the stimulus.

17. The method of claim 13, wherein at least one base signal which is used to create the at least one ramp stimulus is at least one of: a periodic transient stimulus, a periodically modulated tone, and a modulated noise stimulus.

18. The method of claim 17, wherein the base signal is the periodic transient stimulus, and the periodic transient stimulus is presented at a repetition rate that provides an inter-stimulus interval which is an integer sub-multiple of the length of one of the response data epochs.

19. The method of claim 18, wherein performing signal analysis includes the steps of:
   I. computing a spectrogram by shifting a data window across an averaged sweep generated from said accepted response data;
   II. obtaining phase values from the spectrogram for evoked potentials to at least one ramp stimulus; and
   III. obtaining a phase plot from said phase values using the relationship:

$$\theta_a = \theta_c((T_c/L)*360$$

where $\theta_a$ is an actual phase value of a response frequency being measured, $\theta_c$ is a un-corrected phase value of a response frequency being measured in each data window used to generate a spectrogram, $T_c$ is a cumulative time for a total number of points that have occurred in the response data prior to the first point of each data window, and L is a stimulus period of at least one ramping stimulus.

20. The method of claim 13, wherein the at least one ramp stimulus is created using a ramp function that is at least one of the following: a linear ramp, a logarithmic ramp, a multi-slope ramp, and a symmetrical ramp having an upward and downward ramp, the intensity at the end of the upward ramp being substantially similar to the intensity at the beginning of the downward ramp, and with the upward and downward ramps being selected from one of a linear ramp, a logarithmic ramp, and a multi-slope ramp.

21. The method of claim 13, wherein the method to compute an estimate of said patient's threshold for at least said one ramp stimulus is chosen from at least one of the following: a method that utilizes the lowest intensity for which evoked potential amplitudes are not statistically present, a method that utilizes the lowest intensity for which the evoked potential phases are not statistically stable.

22. The method of claim 13 wherein the result data include a spectrogram.

23. The method of claim 13 wherein the result data include the output of a filter configured to allow the processor to measure evoked potentials.

24. The method of claim 13, wherein a method to compute an estimate of said patient's threshold for at least said one ramp stimulus is chosen from one of the following: regression techniques applied only to R-AEP amplitudes which are statistically present, and regression techniques applied only to R-AEP amplitudes which occur over a limited time period or intensity range of the stimulus.

25. The method of claim 13, wherein the at least one ramp stimulus is created using a ramp function that is at least one of the following: a multi-slope ramp; and, a logarithmic ramp.

26. A method for performing a Multiple Intensity Stimulus Test for rapidly evaluating auditory function of a patient by operating a system for performing objective audiometry, the method comprising:

a. operating a processor of the system to acoustically present in a concurrent fashion at least one periodic acoustic stimulus using at least two different intensities to at least one ear of a subject;

b. operating the processor to provide recording of steady-state response data related to the patient's response to the at least two periodic acoustic stimuli;

c. operating the processor to perform signal analysis on said response data to generate result data, and d. operating the processor to calculate upon the result data to statistically evaluate the presence of responses to said at least two different intensities; and e. operating the processor to provide both of the following: a pass/fail result for a screening test and an estimate of the patient's hearing threshold.

27. A method of testing auditory function of a patient, by operating a system for performing objective audiometry, the method comprising:

a. operating a processor of the system to acoustically presenting at least one ramp stimulus having a selected intensity range to at least one ear of the patient;

b. operating the processor to provide recording of response data epochs of ramping evoked potential response data related to the patient's response to said at least one ramp stimulus;

c. operating the processor of the system to classify said response data epochs into accepted response data epochs and rejected response data epochs, wherein a response data epochs is classified as rejected if said response data epoch fails in meeting a homogeneity criteria;

d. operating the processor of the system to perform time-frequency signal analysis on the acceptable response data epochs to generate result data; and, e. operating the processor of the system to calculate upon said result data to compute an estimate of said patient's threshold for at least said one ramp stimulus.

28. The method of claim 27, further comprising performing steps (a)-(e) iteratively, and for each iteration, including an estimate of said patient's threshold in a threshold series, wherein the iterations are continued until said threshold series meets a criterion related to a reliability measure of the threshold estimate.

29. The method of claim 27, further comprising performing steps (a)-(e) iteratively, and on each iteration, including an estimate of said patient's threshold for two or more ramp stimuli in two or more threshold series, wherein the iterations are continued until said two or more threshold series meet a statistical conditional criterion related to a reliability measure of the threshold estimate.

30. The method of claim 27 wherein the result data include at least one of the following: estimates of instantaneous amplitudes and phases of evoked potentials at different moments in time, estimates of instantaneous amplitudes of EEG-noise level estimates at different moments in time, an average of estimates of instantaneous amplitudes of EEG-noise level estimates at different moments in time, estimates of instantaneous statistical probability that evoked potentials are present at different moments in time, and a spectrogram.

31. The method of claim 27, wherein the homogeneity criteria include at least one of the following: intra-sweep homogeneity criteria which are adjusted based upon statistical evaluation of at least one characteristic that is measured for each epoch of data within a sweep, intra-sweep homogeneity criteria which are adjusted based upon at least one characteristic that is measured for an epoch of data within two or more sweeps.

32. The method of claim 31, wherein the at least one characteristic that is measured for an epoch of data is at least one of the following: an estimate for EEG-noise energy, an estimate of signal energy, and an SNR estimate.

33. The method of claim 27, wherein rejected epochs are replaced using at least one of a zero replacement technique, a swapping replacement technique, and a repeating replacement technique.

34. The method of claim 27, wherein the at least one ramp stimulus is created using a ramp function that is at least one of the following: a multi-slope ramp, and a symmetrical ramp having an upward and downward ramp, the intensity at the end of the upward ramp being substantially similar to the intensity at the beginning of the downward ramp.

35. The method of claim 27, further comprising:
f. partitioning a stimulus intensity range into at least two intensity ranges, the number of intensity ranges corresponding to the number of ramp stimuli, and uniquely assigning one of the intensity ranges to each of the ramp stimuli;
g. performing steps a-e iteratively to generate a threshold series for each of the ramp stimuli based on iterative estimates of the patient's threshold and continuing the iterations until the threshold series meets specified criteria; and,
h. using at least one of the threshold series to provide at least one threshold estimate for the patient.

36. The method of claim 35, wherein the several intensity ranges are non-overlapping.

37. The method of claim 27, wherein the method further comprises:
f. selecting a second intensity range for a ramp stimulus based on an estimate of the patient's threshold, the second intensity range being smaller than the intensity range selected in step (a) and
g. performing steps a-e based on the intensity range selected in step (f).

38. The method of claim 37, wherein the intensity range of the second ramp stimulus is chosen to be closer to the intensity range of the ramp stimulus in step (a) if the signal to noise level is low and the intensity range of the second ramp stimulus is chosen to be further away from the intensity range of the ramp stimulus in step (a) if the signal to noise level is high.

39. The method of claim 27, wherein the at least one acoustic stimulus comprises:
a masking stimulus component having a stimulus characteristic which is a carrier signal frequency that is ramped over time, and which is either modulated or unmodulated;
a probe stimulus component having a constant carrier signal frequency and a constant modulation rate; and,
whereby the test comprises a RAMPER Masking Test that provides data about the effect of the masking stimulus component or the probe stimulus component.

40. The method of claim 27, wherein a method to compute an estimate of said patient's threshold for at least said one ramp stimulus is chosen from one of the following: the lowest intensity for which R-AEP amplitudes are not statistically present, the lowest intensity for which the R-AEP phases are not statistically stable, regression techniques, regression techniques applied only to R-AEP amplitudes which are statistically present, and regression techniques applied only to R-AEP amplitudes which occur over a limited time period or intensity range of the stimulus.

41. The method of claim 27, further comprising performing weighted averaging whereby said rejected response data are assigned weights which are combined with acceptable response data.

42. The method of claim 27, further comprising performing steps (a)-(e) iteratively and on each iteration, including an estimate of said patient's threshold for two or more ramp stimuli in two or more threshold series, wherein the iterations are continued until said two or more threshold series meet statistical conditional criteria related to a reliability measure of the threshold estimate.

43. The method of claim 27, further comprising performing steps (a)-(e) iteratively, and on each iteration, including an estimate of said patient's threshold for one or more ramp stimuli in two or more threshold series, wherein the iterations are continued until said two or more threshold series meet statistical conditional criteria related to a reliability measure of the threshold estimate, and wherein each of the threshold series are calculated on at least a portion of the response data.

44. The method of claim 27, wherein the homogeneity criteria include intra-column homogeneity criteria which are adjusted based upon at least one characteristic that is measured for an epoch of data, that is organized within a same column of epochs, said column of epochs containing all accepted epochs that are time locked to a particular portion of a ramp stimulus.

45. The method of claim 27, wherein the method further comprises:
f. using the signal to noise levels of the result data to determine a useful intensity range for a subsequent ramp stimulus;
g. replacing said ramp stimulus with said subsequent ramp stimulus; and,
h. performing steps a-g iteratively to generate a threshold based on iterative estimates of the patient's threshold and continuing the iterations until the threshold series meets a specified criteria.

46. The method of claim 45, wherein the intensity range of the second ramp stimulus is chosen to be closer to the intensity range of the ramp stimulus in step (a) if the signal-to-noise level is low and the intensity range of the second ramp stimulus is chosen to be further away from the intensity range of the ramp stimulus in step (a) if the signal-to-noise level is high.

47. A method of testing auditory thresholds according to a Conditional MASTER Screening Test, by operating a system for performing objective audiometry, the method comprising:
a. operating a processor of the system to presenting at least three acoustic stimuli to at least one ear of a patient;
b. operating the processor to provide recording of steady-state evoked potentials data epochs related to the patient's response to the at least three acoustic stimuli;
c. operating the processor to provide classifying of said evoked potentials data epochs into accepted epochs and rejected epochs on the basis of selected criteria;

d. operating the processor to provide processing of the accepted epochs to determine which evoked potentials are statistically present;

e. operating the processor to repeat steps a-d until a specified criterion has been met; and f. operating the processor to provide to a pass result if at least a specified number of evoked potentials were statistically present and a fail result if less than a specified number of evoked potentials were not statistically present.

48. The method of claim 47, wherein in step d, wherein an SS-AEP is determined to be statistically present when a significance series has been generated for each SS-AEP and the statistical series has successfully met one or more statistical conditional criteria.

49. The method of claim 47, wherein the specified criterion of step e, is based upon normative age appropriate screening-test data and is at least one of: an amount of recording time and a level of background EEG-noise present in the recording.

50. A method of optimizing modulation frequencies used in an audiometric test that provides at least one modulated stimulus to evaluate the auditory system of a patient, by operating a system for performing objective audiometry, the method comprising:

a. operating the processor of the system to provide modulation optimization test stimuli; and operating the processor to provide recording of result data;

b. operating the processor of the system to analyze the result data to derive at least one modulation rate with SNR characteristics meeting a selected criterion; and, c. operating the processor of the system to select and then use using the at least one modulation rate in an objective auditory test which is subsequently performed on the patient.

51. The method of claim 50, wherein the objective auditory test comprises at least one of an ASSR test, a MASTER test, and RAMPER test.

52. The method of claim 50, wherein step (a) comprises:
(i) presenting at least one stimulus to the patient, said stimulus having a modulation rate which changes over time;
(ii) recording evoked response data related to the patient's response to the at least one stimulus; and
(iii) analyzing the evoked response data to produce result data, said result data containing the SNR characteristic for at least 2 modulation frequencies.

53. The method of claim 52, wherein in step (iii) analyzing the evoked response data is accomplished using time frequency analysis.

54. The method of claim 52, wherein step (i) includes presenting the at least one stimulus to the patient at an intensity level that is at least 10 dB above the stimulus intensities for use in a subsequent audiometric test.

55. The method of claim 52, wherein step (i) includes presenting RAMP stimuli to at least one of the left and right ears of the patient.

56. The method of claim 55, wherein the stimuli presented to the left ear differ from those presented to the right ear.

57. A method of performing a Fine Structure Test to evaluate auditory system of a patient comprising:

a. presenting at least one acoustic ramp stimulus to the patient, said ramp stimulus having at least one stimulus characteristic which ramps over time, and wherein said stimulus characteristic is not intensity and is selected to be one of: modulation rate, carrier frequency, and carrier frequency of a masking stimulus;

b. recording evoked response data from the patient to form primary data;

c. performing signal analysis on the primary data, and rejecting primary data sections which do not meet specified homogeneity criteria, to obtain processed data;

d. analyzing the processed data using time-frequency analysis to produce result data;

e. using the result data to evaluate auditory capacities of the auditory system of said patient.

58. The method of claim 57 wherein the at least one acoustic ramp stimulus has a stimulus characteristic which is a modulation rate that is ramped over time whereby the Fine Structure test provides result data about which modulation frequencies evoked larger responses from the patient.

59. The method of claim 57, wherein the at least one acoustic ramp stimulus has a carrier frequency that is ramped over time whereby the Fine Structure test provides data in which the fine structure of the patient's audiogram is derived in relation to carrier frequency.

60. The method of claim 57 wherein the result data include at least one of the following: estimates of instantaneous amplitudes and phases of evoked potentials at different moments in time, estimates of instantaneous amplitudes of EEG-noise level estimates at different moments in time, an average of estimates of instantaneous amplitudes of EEG-noise level estimates at different moments in time, estimates of instantaneous statistical probability that R-AEPs are present at different moments in time, and a spectrogram.

* * * * *